United States Patent [19]

Wilkening

[11] Patent Number: 5,202,434
[45] Date of Patent: Apr. 13, 1993

[54] 8A-AZA-8A-HOMOERYTHROMYCIN LACTAMS

[75] Inventor: Robert R. Wilkening, Maplewood, N.J.

[73] Assignee: Merck & Co., Inc., Rahway, N.J.

[21] Appl. No.: 856,267

[22] Filed: Mar. 27, 1992

Related U.S. Application Data

[63] Continuation-in-part of Ser. No. 681,223, Apr. 5, 1991, abandoned.

[51] Int. Cl.$^5$ .................. C07D 267/00; A61K 31/395
[52] U.S. Cl. ...................................... 540/454; 514/183
[58] Field of Search .......................................... 540/454

[56] References Cited

PUBLICATIONS

Paur, et al., *SCH 23831, a novel macrolide from Micromonospora rosaria*, Tetrahedron Letters, No. 30, pp. 2767–2770 (Jul. 1979).

Primary Examiner—Robert T. Bond
Attorney, Agent, or Firm—Frank P. Grassler; Joseph F. DiPrima

[57] ABSTRACT

Lactams of the general structural formula:

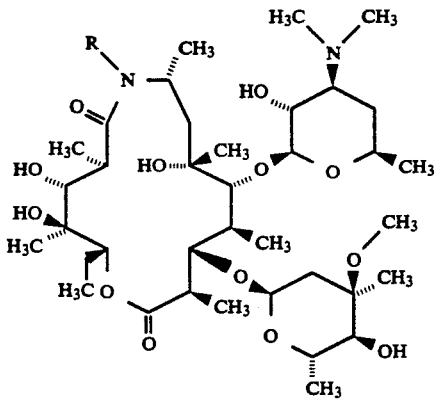

wherein R is hydrogen or $C_{1-10}$ alkyl. These compounds are macrolides useful as antibiotics and as intermediates for the synthesis of other macrolide antibiotics.

4 Claims, No Drawings

8A-AZA-8A-HOMOERYTHROMYCIN LACTAMS

This is a continuation-in-part of prior application Ser. No. 07/681,223, filed Apr. 5, 1991, abandoned.

BACKGROUND OF THE INVENTION

The present invention relates to a novel group of chemical compounds having antibacterial activity, which are useful in the therapy of bacterial infections in mammals. The compounds themselves are also useful as intermediates in the synthesis of other antibacterial compounds. More specifically, the invention relates to derivatives of the well-known macrolide antibiotic, erythromycin A, the compound of the structure:

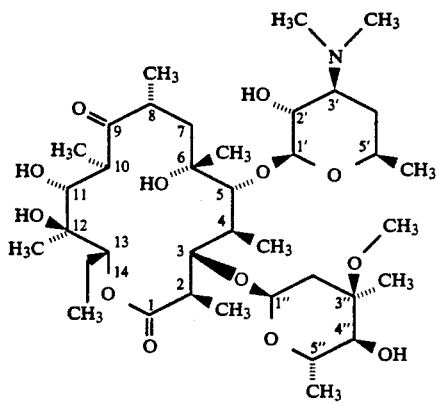

Even more specifically, the invention relates to the compounds of the structure:

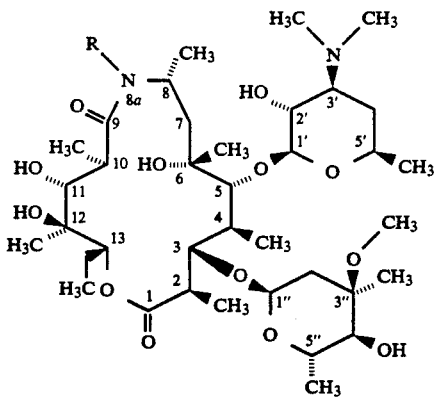

wherein R is hydrogen or $C_{1-10}$ alkyl.

The present invention also provides for novel pharmaceutical compositions and methods of their use as antibiotic agents.

SUMMARY OF THE INVENTION

The present invention relates to novel compounds, cyclic lactams of 15 membered macrolide antibiotics having the formula.

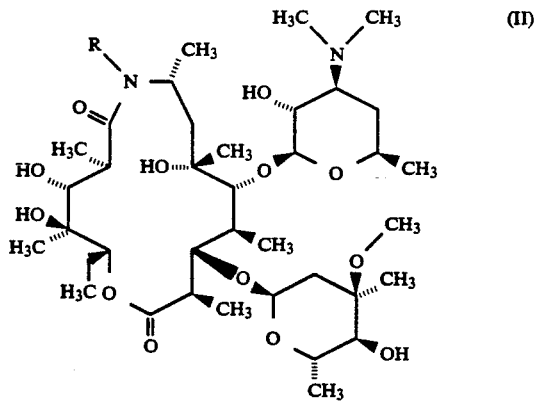

where R is hydrogen or $C_{1-10}$ alkyl.

The invention includes the pharmaceutically acceptable salts and esters of the compounds shown above. Such salts are generally prepared as acid addition salts by combining the compound of formula II with a stoichiometric amount of an appropriate acid in an inert solvent. The salt is then recovered by solvent evaporation or by filtration if the salt precipitates spontaneously, or by precipitation using a co-solvent or nonpolar co-solvent followed by filtration.

Representative salts and esters include the following:

| | |
|---|---|
| Acetate | Isothionate |
| Benzenesulfonate | Lactate |
| Benzoate | Lactobionate |
| Bicarbonate | Laurate |
| Bisulfate | Malate |
| Bitartrate | Maleate |
| Borate | Mandelate |
| Bromide | Mesylate |
| Calcium Edetate | Methylsulfate |
| Camsylate | Mucate |
| Carbonate | Napsylate |
| Chloride | Nitrate |
| Clavulanate | Oleate |
| Citrate | Oxalate |
| Edetate | Pamoate (Embonate) |
| Edisylate | Palmitate |
| Estolate | Pantothenate |
| Esylate | Phosphate/diphosphate |
| Ethylsuccinate | Polygalacturonate |
| Fumarate | Salicylate |
| Gluceptate | Stearate |
| Glucoheptonate | Subacetate |
| Gluconate | Succinate |
| Glutamate | Tannate |
| Glycollylarsanilate | Tartrate |
| Hexylresorcinate | Teoclate |
| Hydrabamine | Tosylate |
| Hydrobromide | Triethiodode |
| Hydrochloride | Valerate |
| Iodide | |

DETAILED DESCRIPTION OF THE INVENTION

The term "pharmacologically effective amount" shall mean that amount of a drug or pharmaceutical agent that will elicit the biological or medical response of a tissue, system or animal that is being sought by a researcher or clinician.

The term "antibiotically effective amount" shall mean that amount of an antibiotic compound that will achieve a level of antibacterial activity at the site of infection that is sufficient to inhibit the bacteria in a manner that allows the host organism to overcome the infection.

The term "alkyl" shall mean cyclic or linear straight or branched chain alkane of one to ten carbon atoms, or cyclic or linear straight or branched chain alkene of two to ten carbon atoms with one or more degrees of unsaturation.

The compounds of formula II can be prepared readily according to the following detailed descriptions and examples or modifications thereof using readily available starting materials, reagents and conventional synthesis procedures. The overall process is illustrated in flow sheet I wherein the steps leading to (II) are explicitly described below. In these reactions, it is also possible to make use of variants which are themselves known to those of ordinary skill in this art, but which are not mentioned in greater detail.

FLOW SHEET I

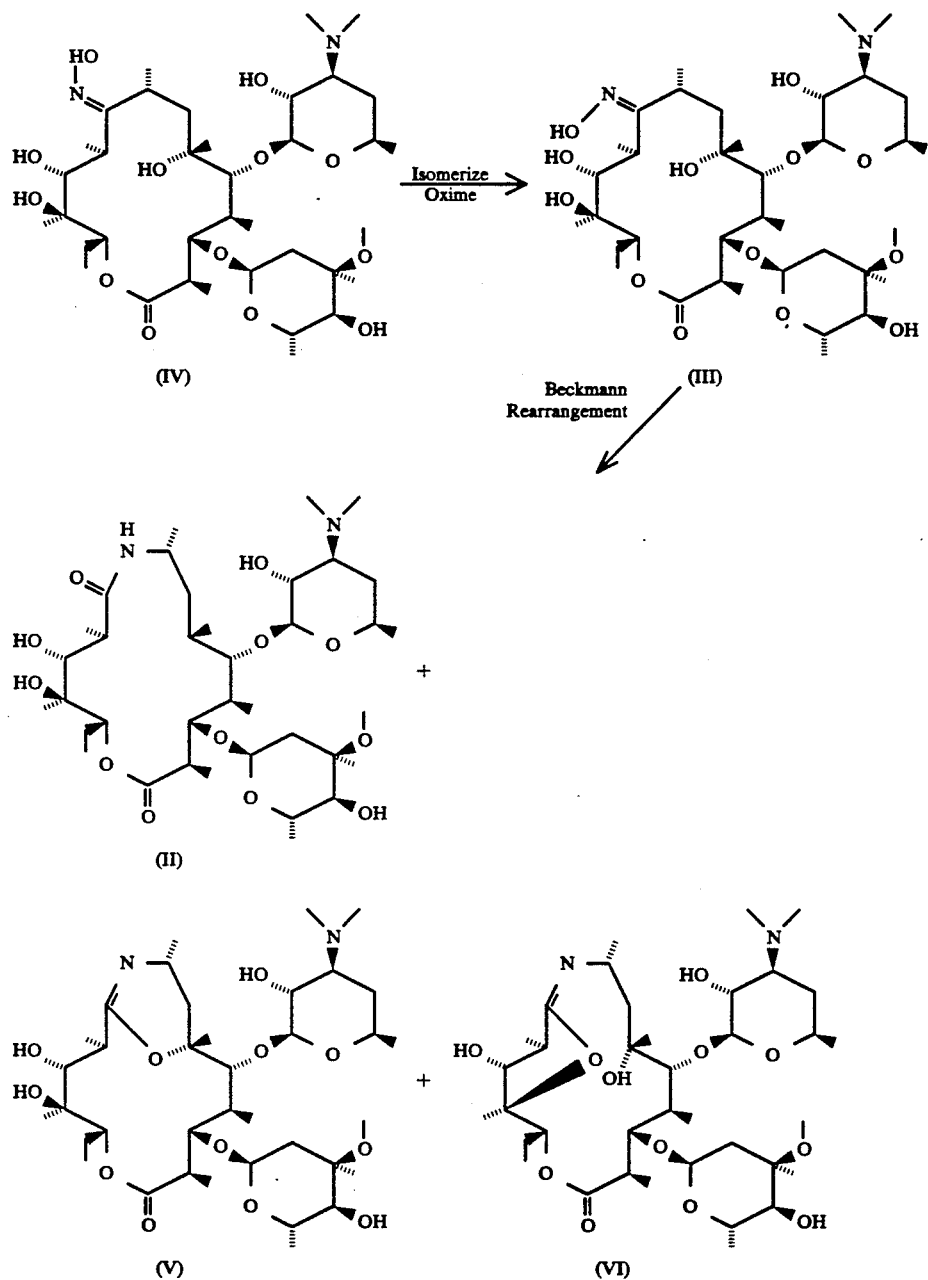

Isomerization of (9E)-9-Deoxo-9-hydroxyiminoery-thromycin A to the (9Z) isomer

In a single step procedure, (9Z)-9-deoxo-9-hydroxyimininoerythromycin A of the structure:

(III)

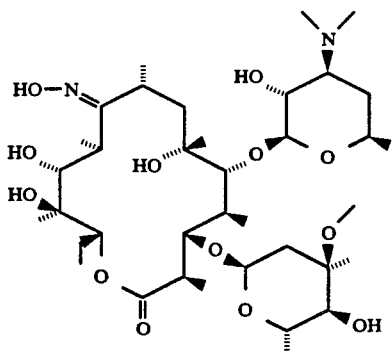

is obtained by reacting a (9E)-9-deoxo-9-hydroxyimino-erythromycin A of the structure:

(IV)

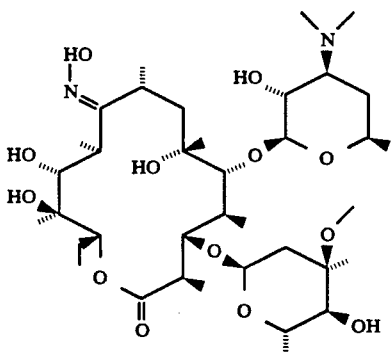

with a base in the presence of a protic or an aprotic solvent. Preferably, the base is an alkali metal hydroxide and the solvent is an alcohol. Most preferably, the base is lithium hydroxide (as the monohydrate) and the solvent is ethanol.

Optimization of the method of the isomerization step requires a base sufficient to substantially deprotonate the hydroxyimino group of (IV). Furthermore, the oxime anion must be reasonably stable under the reaction conditions for the time period required to complete the isomerization process.

Upon addition of the base to (IV), an equilibrium condition is created as shown in the following equation:

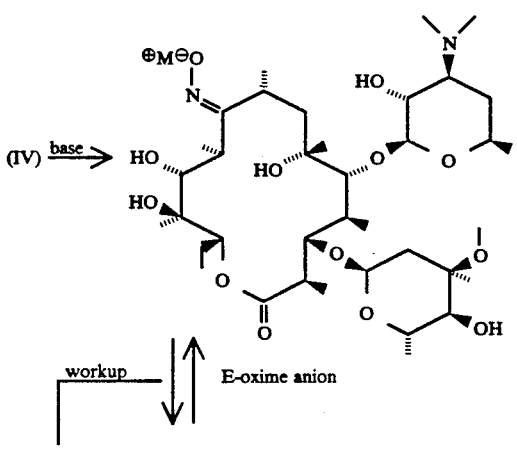

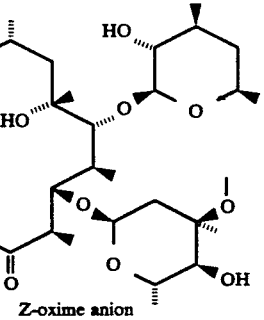

↓

E-oxime (IV)
+
Z-oxime (III)

where ⊕M is a suitable couterion

The workup performed on the anions includes protonation of the oxime anions to give the neutral oxime product mixture from which the desired Z-isomer is isolated by crystallization or by chromatography followed by crystallization.

The relative amounts of E and Z oxime anions (and neutral oximes after the workup) in the equilibrium mixture can be controlled and depends on a number of factors. These include (a) the strength and quantity of the base reagent, (b) the size and polarizability of the counterion $+M$, (c) the reaction solvent, and (d) the reaction temperature.

Suitable bases include hydroxides, alkoxides, carbonates, metal amides, amines and metal hydrides.

The following list of reagents is given to illustrate suitable bases and solvents, although the list is not to be taken as exhaustive and other bases and solvents known to those of ordinary skill in the art are not excluded. Preferred bases and solvents are indicated by an asterisk and most preferred bases are indicated by a dagger.

| | | Bases |
|---|---|---|
| 1. | Hydroxides | |
| | * † LiOH | lithium hydroxide |
| | * † NaOH | sodium hydroxide |
| | *KOH | potassium hydroxide |
| | CsOH | cesium hydroxide |
| | Ca(OH)$_2$ | calcium hydroxide |
| | Mg(OH)$_2$ | magnesium hydroxide |
| | *Me$_4$NOH | tetramethylammonium hydroxide |
| | BnMe$_3$NOH | benzyltrimethylammonium hydroxide |
| | Et$_4$NOH | tetraethylammonium hydroxide |
| | Bu$_4$NOH | tetrabutylammonium hydroxide |
| 2. | Alkoxides | |
| | * † LiOMe | lithium methoxide |
| | * † LiOEt | lithium ethoxide |
| | LiOiPr | lithium isopropoxide |
| | LiOnBu | lithium n-butoxide |
| | LiOsBu | lithium sec-butoxide |
| | * † NaOMe | sodium methoxide |
| | * † NaOEt | sodium ethoxide |
| | NaOPr | sodium n-propoxide |
| | NaOiPr | sodium iso-propoxide |
| | NaOnBu | sodium n-butoxide |
| | NaOsBu | sodium sec-butoxide |
| | NaOtBu | sodium tert-butoxide |
| | NaOSiMe$_3$ | sodium trimethylsilanoate |
| | KOMe | potassium methoxide |
| | *KOEt | potassium ethoxide |
| | KOtBu | potassium tert-butoxide |
| | KOSiMe$_3$ | potassium trimethylsilanoate |
| | KOsBu | potassium sec-butoxide |
| | CsOtBu | cesium tert-butoxide |

| Bases | |
|---|---|
| Ca(OMe)$_2$ | calcium methoxide |
| *Mg(OEt)$_2$ | magnesium ethoxide |
| Ti(OEt)$_4$ | titanium (IV) ethoxide |
| Ti(OiPr)$_4$ | titanium (IV) isopropoxide |
| BnMe$_3$NOMe | benzyltrimethylammonium-methoxide |
| 3. Carbonates | |
| K$_2$CO$_3$ | potassium carbonate |
| *Cs$_2$CO$_3$ | cesium carbonate |
| Na$_2$CO$_3$ | sodium carbonate |
| 4. Amides (for use in aprotic solvents) | |
| LiNH$_2$ | lithium amide |
| LiNMe$_2$ | lithium dimethylamide |
| *LiNiPr$_2$ | lithium diisopropylamide |
| LiN(C$_6$H$_{11}$)$_2$ | lithium dicyclohexylamide |
| LiN(SiMe$_3$)$_2$ | lithium bis(trimethylsilyl) amide |
| NaNH$_2$ | sodium amide |
| KN(SiMe$_3$)$_2$ | potassium bis(trimethylsilyl) amide |
| 5. Amines | |
| *TMG | 1,1,3,3-tetramethyl guanidine |
| DBU | 1,8-diazabicyclo[5.4.0]undec-7-ene |
| proton sponge | 1,8-bis(dimethylamino)-naphthalene |
| 6. Hydrides (for use in aprotic solvents) | |
| LiH | lithium hydride |
| *NaH | sodium hydride |
| KH | potassium hydride |
| 7. Solvents | |
| a. Protic | |
| H$_2$O (generally used in combination with an alcohol solvent) | |
| *†MeOH | methanol |
| *†EtOH | ethanol |
| *iPrOH | isopropanol |
| n-BuOH | normal-butanol |
| s-BuOH | sec-butanol |

| Bases | |
|---|---|
| t-BuOH | tert-butanol |
| b. Aprotic | |
| i. Nonpolar (as a group, these are generally used in combination with a protic or polar solvent) | |
| Et$_2$O | diethyl ether |
| THF | tetrahydrofuran |
| DME | dimethoxyethane |
| PhMe | toluene |
| CH$_2$Cl$_2$ | dichloromethane |
| CHCl$_3$ | chloroform |
| ii. Polar | |
| *DMF | dimethylformamide |
| DMAC | dimethylacetamide |
| DMI | 1,3-dimethyl-2-imidazolidinone |
| *NEP | 1-ethyl-2-pyrrolidinone |
| *NMP | 1-methyl-2-pyrrolidinone |
| HMPA | hexamethylphosphoramide |
| MeNO$_2$ | nitromethane |
| *MeCN | acetonitrile |
| dioxane | |
| pyridine | |
| DMSO | dimethyl sulfoxide |

Preferably, the isomerization reaction is carried out at a concentration of 1–25% w/v of E-oxime to solvent, and most preferably at 10% w/v. The amount of base used is preferably 1.0–10.0 molar equivalents based on the amount of starting E-oxime, more preferably 1.0–3.0 molar equivalents, and most preferably 2.0 molar equivalents. The reaction is generally run at a temperature of from 0° C. to 80° C., and more preferably at 22°–25° C. The reaction can be allowed to run for 0.5 hour to 20 days, but most preferably is carried out over 20–24 hours.

Beckmann Rearrangement of (9Z)-9-Deoxo-9 hydroxyiminoerythromycin A

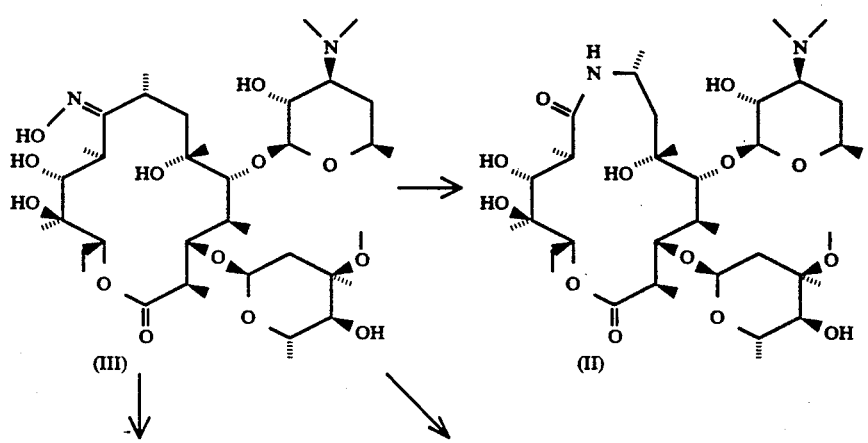

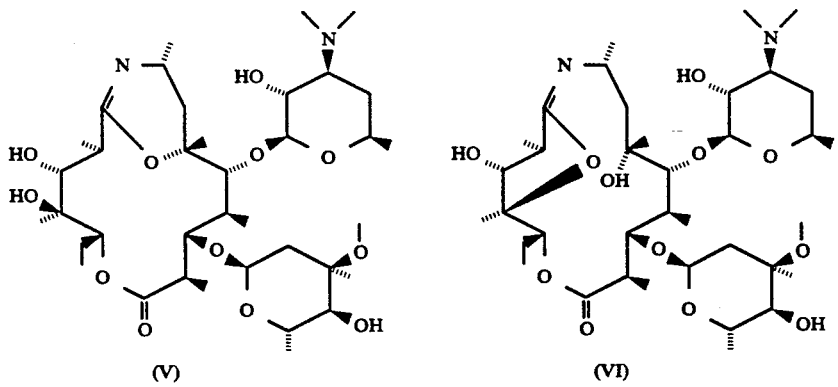

(V)             (VI)

The conversion of (9Z)-9-deoxo-9-hydroxyiminoerythromycin A (III) to the 8a-aza-8a-homoerythromycin products (II), (V) and (VI) is accomplished by means of the Beckmann rearrangement (see "Comprehensive Organic Chemistry", I. O. Sutherland (Ed.), Pergamon Press, N.Y. 1979, Vol. 2, pgs. 398–400 and 967–968). In general, the Beckmann rearrangement of ketoximes leads to carboxamides and, of particular relevance in cyclic systems, to ring expanded lactams. The mechanism of the rearrangement involves initial conversion of the oxime hydroxyl group to a leaving group which is then lost with concomitant migration of the oxime carbon substituent that is situated anti to the leaving group. In aqueous media, the intermediate nitrilium cation thus formed usually reacts with water to afford the amide product. The nitrilium intermediate can also be trapped by other suitable nucleophiles thereby leading to imino products such as imidates and amidines.

The Beckmann rearrangement has been accomplished under a variety of acidic, neutral and basic conditions. Common acidic reagents that promote the transformation include concentrated sulfuric acid, polyphosphoric acid, thionyl chloride, phosphorous pentachloride, sulfur dioxide, and formic acid. These reagents are generally not applicable to the rearrangement of oxime (III) due to the sensitivity of the macrolide molecule, and especially the cladinose sugar residue, to acidic conditions. Efficient Beckmann rearrangement also occurs by heating the oxime with silica gel in xylene or under mildly basic conditions by heating the oxime in hexamethylphosphoramide. These conditions are not particularly valuable for the conversion of (III) to products (II), (V) and (VI) due to competing isomerization of the oxime function under the reaction conditions.

A preferred method for effecting the Beckmann rearrangement involves initial O-sulfonylation of the oxime group with an alkylsulfonyl halide, arylsulfonyl halide or arylsulfonic anhydride. The intermediate oxime sulfonate thus formed can be isolated or, as more commonly practiced, converted in situ to the rearranged products. The sulfonylation and rearrangement reactions are generally performed in the presence of an organic or inorganic base. This method is particularly valuable for the conversion of oxime (III) to the rearranged products (II), (V), and (VI).

Preferred sulfonylating reagents for effecting the rearrangement of oxime (III) include methanesulfonyl chloride, benzenesulfonyl chloride, 4-acetamidobenzenesulfonyl chloride, p-toluenesulfonyl chloride, benzenesulfonic anhydride, and p-toluenesulfonic anhydride. The reaction is carried out in the presence of an inorganic base such as sodium bicarbonate or potassium carbonate, or in the presence of an organic base such as pyridine, 4-dimethylaminopyridine, triethylamine, or N,N-diisopropylethylamine. Suitable solvents include aqueous mixtures such as aqueous acetone or aqueous dioxane and organic solvents such as dichloromethane, chloroform, ethyl acetate, diethyl ether, tetrahydrofuran, toluene, acetonitrile, and pyridine. Mixtures of organic solvents, especially those containing pyridine, are highly useful. The reaction is generally performed using 1–3 molar equivalents of the sulfonylating agent and one or more molar equivalents of base at a reaction temperature of $-20°$ C. to $50°$ C. Pyridine is often used as both solvent and base.

The distribution of products resulting from Beckmann rearrangement of oxime (III) depends on the particular reaction conditions employed. For example, when the rearrangement is effected with p-toluenesulfonyl chloride and sodium bicarbonate in aqueous acetone, the major products are the lactam (II) and the 6,9-bridged iminoether (V). When the reaction is conducted under anhydrous conditions such as p-toluenesulfonyl chloride in pyridine, the major products are the 6,9-bridged and 9,12-bridged iminoethers (V) and (VI).

The products of the Beckmann rearrangement of oxime (III) are conveniently purified by chromatographic methods. For example, the lactam (II) is easily separated from iminoether (V) using column chromatography on silica gel or by reverse phase, high-pressure liquid chromatography. Products (V) and (VI) can also be separated by chromatographic methods, and the (VI) thus obtained can be further purified by crystallization from nitromethane.

As previously noted, Beckmann rearrangement of oxime (III) under anhydrous conditions leads to a product mixture comprised of the 6,9- and 9,12-bridged iminoethers (V) and (VI). The 9,12-bridged product, which is formed by internal trapping of the intermediate nitrilium species by the hydroxyl group at C-12, is initially isolated as a mixture of major and minor forms. The initial mixture of isomers equilibrates at room temperature, both in solution or on storing as a crude foam, to approximately a 1:1 mixture of isomers. The first-formed, major isomer can be isolated from the mixture by crystallization from nitromethane solution.

FLOW SHEET II
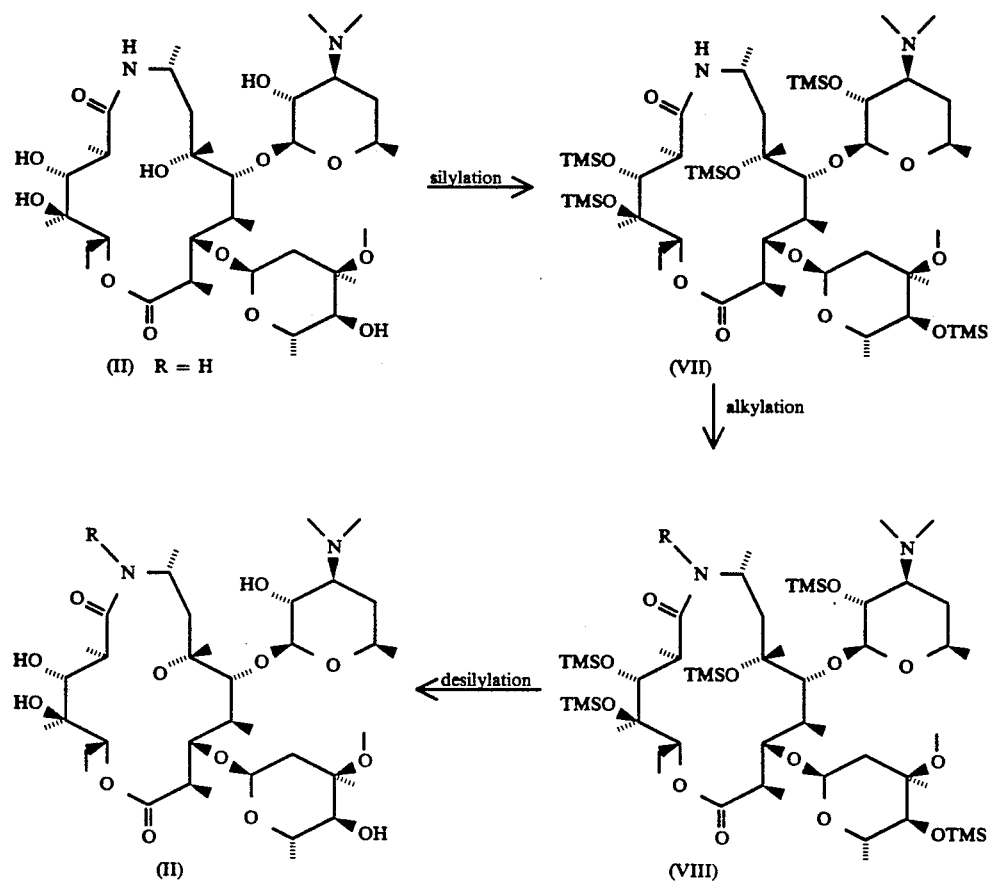
FLOW SHEET III
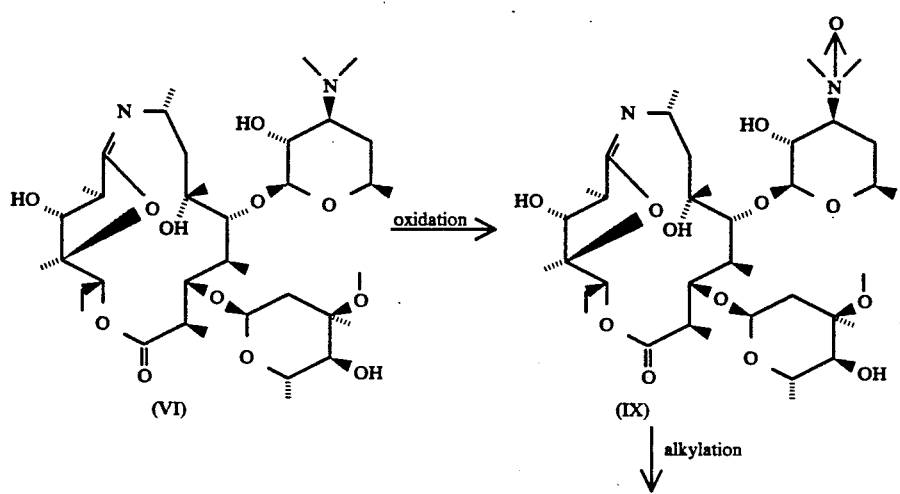

-continued
FLOW SHEET III
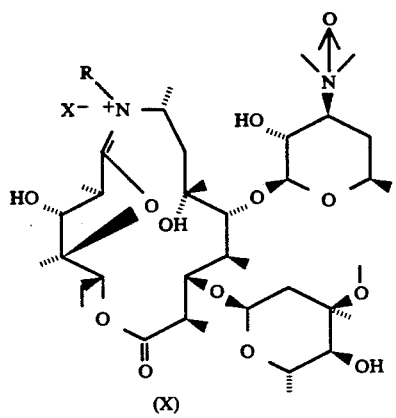
(X)
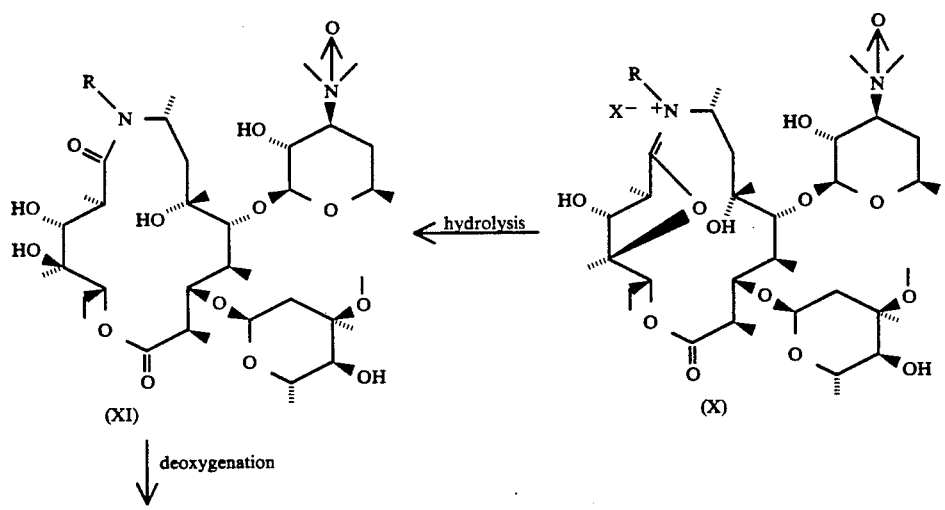
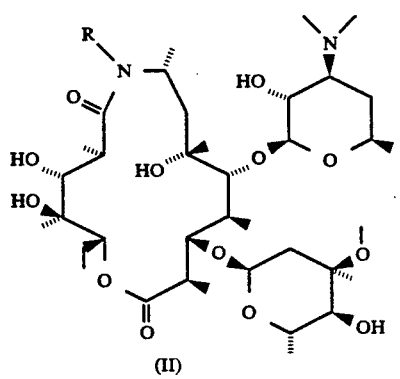
(II)

FLOW SHEET IV
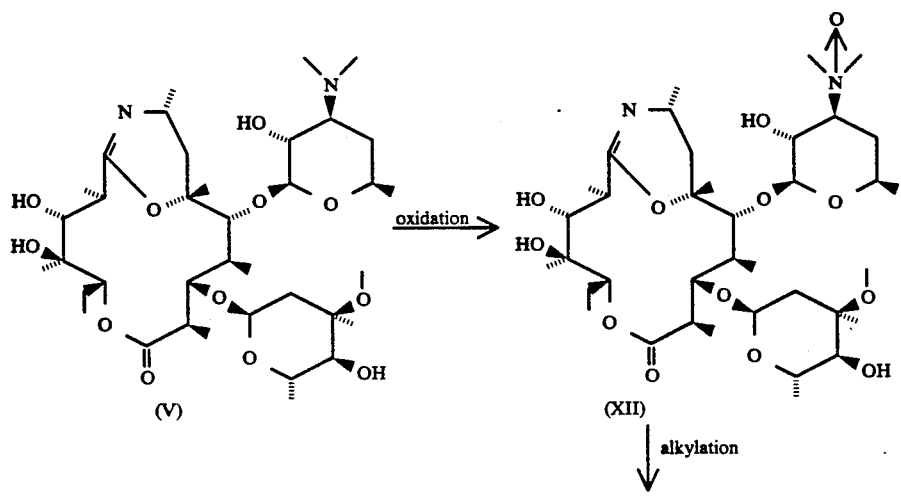
(V) —oxidation→ (XII)
↓ alkylation
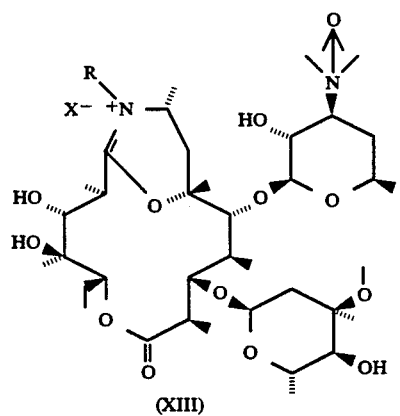
(XIII)
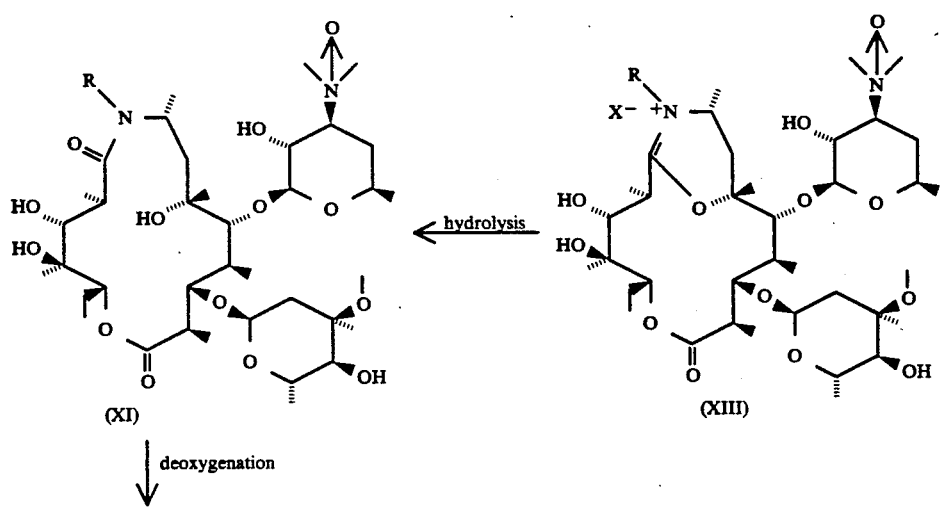
(XI) ←hydrolysis— (XIII)
↓ deoxygenation -continued
FLOW SHEET IV

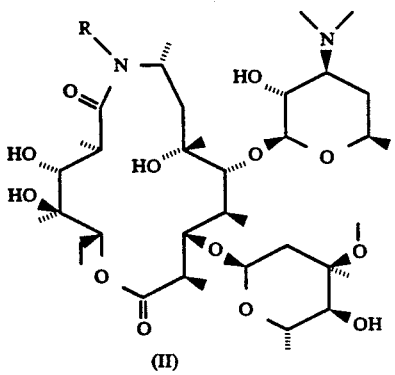

(II)

The compounds of formula (II) wherein R is a 1-10 carbon alkyl substituent are readily prepared by the methods outlined in Flow Sheets II, III, and IV.

In Flow Sheet II, the unsubstituted lactam (II, R=H) is first silylated in order to protect the hydroxyl groups in the subsequent alkylation step. O-Silylation is readily accomplished with a variety of reagents and generally leads to products in which three to five of the available hydroxyl groups are covered. The degree of silylation depends on the exact conditions employed and on the quantity of silylating agent used. For example, using excess trimethylsilyl trifluoromethanesulfonate in dichloromethane containing 2,6-lutidine or using excess bis(trimethylsilyl) trifluoroacetamide (BSTFA) in pyridine provides the persilylated intermediate (VII).

N-Alkylating is accomplished by treating the slylated intermediate (VII) with a strong base and an alkylating agent. Suitable bases include, but are not limited to, potassium hydroxide, sodium hydroxide, sodium hydride and lithium diisopropylamide. The alkylating agent is of the form RX wherein X represents a leaving group such as bromide, iodide, methanesulfonate (OMs), p-toluenesulfonate (OTs) or trifluormethanesulfonate (OTf). The alkylation reaction is usually carried out in a nonaqueous solvent such as tetrahydrofuran, diethyl ether, toluene, dimethylsulfoxide, dimethylformamide, dimethoxyethane, or mixtures thereof. A particularly preferred alkylation method uses sodium hydride in dimethylformamide to deprotonate the lactam group followed by addition of an alkyl iodide or bromide to introduce the desired alkyl substituent.

The resulting N-alkylated, O-silylated intermediate (VII) is then desilylated using any one of a number of well known techniques. Representative methods include hydrolysis in aqueous acetic acid or the use of fluoride based reagents such as hydrogen fluoride in pyridine or, preferably, tetrabutylammonium fluoride in tetrahydrofuran. The resulting final products (II) are conveniently purified by chromatography on silica gel, by direct crystallization, or by a combination of chromatography and crystallization.

An alternative method of introducing alkyl substitution at position 8a of the aglycone ring is illustrated in Flow Sheets III and IV. The overall chemistry, which involves 1) protection of the desosamine dimethlyamino group by conversion to its oxide, 2) N-alkylation of the imidate group, 3) hydrolysis of the alkylated imidate to a lactam group, and 4) deoxygenation of the sugar N-oxide, is identical in the two schemes. The schemes differ only as to the specific structure of the starting iminoether; that is, whether the 9,12-bridged intermediate (VI) or the 6,9-bridged intermediate (V) is used. Since the reactions are equivalent in both schemes, the discussion below is limited to Flow Sheet III, with the understanding that the discussion also applies to the transformations illustrated in Flow Sheet IV.

The initial step in Flow Sheet III involves the protection of the desosamine dimethylamino group to alkylation by its conversion to the corresponding N-oxide derivative (IX). This transformation is readily accomplished using oxidizing agents such as m-chloroperbenzoic acid in dichloromethane or aqueous hydrogen peroxide in methanol. The imidate group of the resulting product is N-alkylated using a powerful alkylating agent in an inert organic solvent. Suitable combinations include alkyl iodides, alkyl trifluoromethanesulfonates and trialkyloxonium salts in solvents such as dichloromethane, acetonitrile and nitromethane. The resulting quaternized imidate (X) is easily hydrolyzed under basic conditions to the N-substituted lactam intermediate (XI). Representative reagents for the (X) to (XI) conversion include concentrated aqueous ammonia or sodium hydroxide in aqueous ethanol. The final step of Flow Sheet III involves the deoxygenation of the desosaminyl N-oxide group. This transformation is accomplished using a deoxygenating reagent such as triphenylphosphine or by hydrogenation in the presence of a palladium or platinum catalyst. As noted before, the final products (II) can be purified by chromatography or by crystallization.

As antibiotics, the compounds of formula (II) can be administered in such oral dosage forms as tablets, capsules, pills, powders, granules, elixirs, tinctures, suspensions, syrups and emulsions. Likewise, they may also be administered in intravenous, intraperitoneal, subcutaneous or intramuscular form, all using forms well known to those of ordinary skill in the pharmaceutical arts. In general, the preferred form of administration is oral. An effective but non-toxic amount of the compound can be employed as a mammalian antibiotic.

The dosage regimen utilizing the compounds of formula (II) is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Dosages of the compounds of formula (II), when used for the indicated effects, will range between about 0.2 mg per kg of body weight per day (mg/kg/day) to about 120 mg/kg/day and preferably 4-50 mg/kg/day. Advantageously, the compound may be administered in a single daily dose, or the total daily dosage may be administered in divided doses of two, three or four times daily.

Furthermore, the compounds of formula (II) can be administered in topical, otic or ophthalmic form via use of suitable vehicles.

In the methods of using the compounds (II), they can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups, and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol, and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweetners, natural and synthetic gums such as acacia, tragacanth or sodium alginate, carboxymethylcellulose, polyethylene glycol, waxes, and the like. Disintegrators include, without limitation, starch, methyl cellulose, agar, bentonite, xanthan gum, and the like.

The compounds of formula (II) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (II) may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the compounds of formula (II) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following examples further illustrate details for the practice of the invention. Those skilled in the art will readily understand that known variations, when taken with the alternative bases and solvents taught above, can be used.

EXAMPLE 1

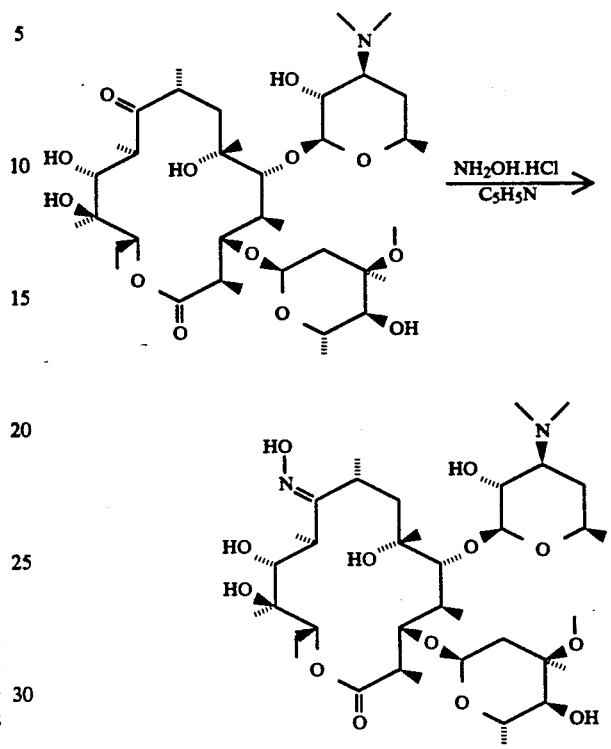

Preparation of
(9E)-9-Deoxo-9-hydroxyiminoerythromycin A

Hydroxylamine hydrochloride (224 g, 3.23 mol) was added to a solution of erythromycin A (100 g, ca. 95% pure, 0.129 mol, available from Aldrich Chemical, Inc., Milwaukee, Wis.) in pyridine (500 mL). The resulting mixture was stirred at room temperature for 27 hours, and then concentrated under vacuum at ca. 40° C. The semi-solid residue was kept under high vacuum overnight, then stirred with ethanol (600 mL) for 15 minutes and filtered. The collected solids were washed with hot (50° C.) ethanol. The combined filtrate and washing was evaporated under vacuum to a pale blue foam. The foam was shaken with water (850 mL) to give a thick emulsion which was stirred rapidly at room temperature for 2.5 hours to give a filterable precipitate. The precipitate was collected, washed with water (150 mL), and dried under vacuum to give a white solid (117.7 g).

The crude oxime hydrochloride was suspended in 5% aqueous sodium bicarbonate (1000 mL) and methylene chloride (1000 mL), and the mixture was stirred while the pH was adjusted to 9.5 by addition of 5N aqueous sodium hydroxide. The layers were separated and the aqueous portion was extracted with ethyl acetate (500 mL) and ethyl ether (500 mL). The combined organic layer and extracts were dried over sodium sulfate, filtered, and evaporated under vacuum to a white solid (92.3 g). The solid was dissolved in hot ethyl acetate (250 mL), and the solution diluted with hot hexanes (400 mL) and left overnight in a refrigerator. The crystals of (9E)-9-deoxo-9-hydroxyiminoerythromycin A were collected, washed with ice-cold hexane (250 mL), and dried under vacuum to afford a white solid (88.5 g).

IR (CH$_2$Cl$_2$) 3560, 3400 (br), 2980, 2950, 1735, 1460, 1389, 1165, 1110, 1085, 1050, and 1010 cm$^{-1}$.

$^1$H NMR (CDCl$_3$) δ 5.05 (dd, H-13), 4.90 (d, H-1''), 4.38 (d, H-1'), 4.01 (m, H-5''), 3.99 (d, H-3), 3.74 (m, H-8), 3.66 (s, H-11), 3.54 (d, H-5), 3.45 (m, H-5'), 3.28 (s, OCH$_3$), 3.23 (dd, H-2'), 2.96 (t, H-4''), 2.87 (m, H-2), 2.64 (q, H-10), 2.43 (m, H-3'), 2.32 (d, H-2''eq), 2.27 (s, N(CH$_3$)$_2$), 1.98 (m, H-4), 1.87 (m, H-14a), 1.63 (m, H-4'eq), and 1.46 (s, 6-CH$_3$).

$^1$H NMR (CD$_3$OD) δ 5.19 (dd, H-13), 4.48 (d, H-1'), 4.15 (dq, H-5''), 3.98 (d, H-3), 3.76 (m, H-8), 3.70 (m, H-5'), 3.67 (s, H-11), 3.58 (d, H-5), 3.33 (s, OCH$_3$), 3.23 (dd, H-2'), 3.01 (d, H-4''), 2.92 (m, H-2), 2.72 (m, H-10), 2.70 (m, H-3'), 2.43 (d, H-2''eq), 2.33 (s, N(CH$_3$)$_2$), 2.01 (m, H-4), 1.88 (m, H-14a), 1.72 (m, H-4'eq), 1.58 (dd, H-2''b), 1.48 (m, H-14ax), 1.45 (s, 6-CH$_3$), 1.26 (d, 5''-CH$_3$), 1.23 (s, 3''-CH$_3$), 1.14 (s, 12-CH$_3$), 1.10 (d, 4-CH$_3$), 1.05 (d, 8-CH$_3$), and 0.84 (t, CH$_2$CH$_3$).

$^{13}$C NMR (CDCl$_3$) δ 175.3, 171.3, 103.1, 96.3, 83.5, 80.3, 78.1, 77.1, 75.1, 74.3, 72.6, 71.2, 70.9, 68.8, 65.4, 65.3, 49.4, 44.6, 40.3, 38.8, 37.8, 35.1, 32.6, 29.2, 27.0, 25.4, 21.5, 21.3, 18.7, 18.6, 16.3, 14.3, 10.6, and 9.3.

$^{13}$C NMR (CD$_3$OD) δ 177.5, 171.6, 104.0, 98.0, 84.2, 81.2, 79.3, 78.3, 76.3, 74.2, 72.9, 72.2, 69.0, 66.7, 65.2, 50.0, 46.3, 40.7, 39.3, 36.2, 32.0, 27.4, 26.7, 22.3, 22.0, 21.6, 19.3, 19.1, 17.3, 16.6, 14.8, 11.2, and 10.2.

EI Mass Spectrum, m/z 748, 590, 574, 462, 431, 416, 398, 174, 159, 158, and 116.

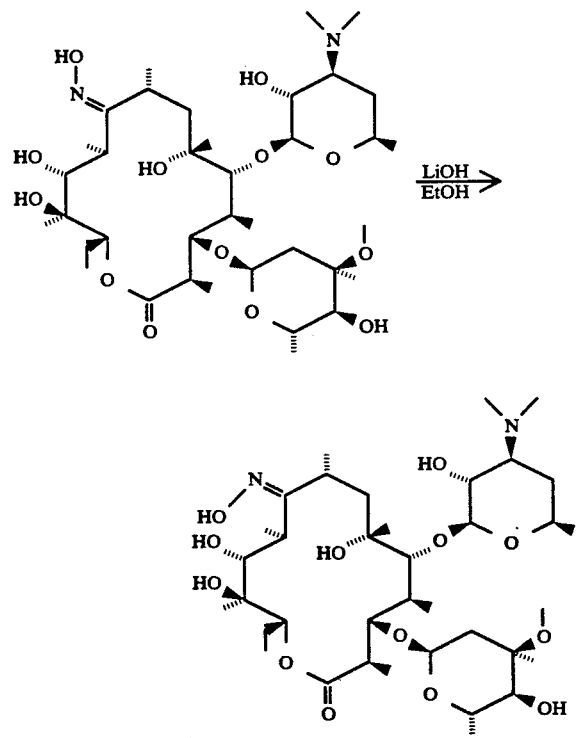

Conversion of
(9E)-9-Deoxo-9-hydroxyiminoerythromycin A to
(9Z)-9-Deoxo-9-hydroximinoerythromycin A Method 1

(9E)-9-Deoxo-9-hydroxyiminoerythromycin A (20.0 g, 26.7 mmol) was added to a stirred solution of lithium hydroxide monohydrate (2.25 g, 53.5 mMol) in absolute ethanol (200 mL). The solution was blanketed with nitrogen and stirred overnight at room temperature. The solvents were evaporated under vacuum and the residue was partitioned between ethyl acetate (200 mL) and brine (120 mL). The pH of the mixture was adjusted from 11 to 9.3 with 2N hydrochloric acid. The ethyl acetate was removed and the brine was re-extracted with more ethyl acetate (2×200 mL). The combined ethyl acetate extracts were washed with brine (100 mL), dried with anhydrous magnesium sulfate, filtered and evaporated under vacuum to a foam (ca. 20 g).

The crude oxime mixture was dissolved in methylene chloride (220 mL) and stirred for 1 hour at room temperature to give a filterable, white solid (18.7 g). This material was dissolved in ethyl acetate (100 mL), diluted with nitromethane (100 mL), and 50 mL of solvent was evaporated under vacuum. Additional nitromethane (50 mL) was added and 80 mL of solvent was evaporated under vacuum. The solution was seeded with the (9Z)-isomer and stirred at room temperature for 3 hours. The resulting suspension was filtered and the solids were rinsed with nitromethane (20 mL) and dried under a stream of nitrogen to afford (9Z)-9-deoxo-9-hydroxyiminoerythromycin A (14.8 g, 74% yield) as a white solid.

MP 157°–164° C.

IR (CHCl$_3$) 3680, 3435 (br), 2970, 2940, 1725, 1455, 1375, 1345, 1165, 1105, 1085, 1045, 1005, and 950 cm$^{-1}$.

$^1$H NMR (CDCl$_3$) δ 5.01 (dd, H-13), 4.87 (d, H-1''), 4.40 (d, H-1'), 3.98 (m, H-3 and H-5''), 3.80 (s, H-11), 3.49 (m, H-5 and H-5'), 3.27 (s, OCH$_3$), 3.21 (dd, H-2'), 2.99 (m, H-4''), 2.8 (m, H-8, H-2 and H-10), 2.74 (m, H-10), 2.43 (m, H-3'), 2.32 (d, H-2''eq), 2.27 (s, N(CH$_3$)$_2$), 1.91 (m, H-4), 1.87 (m, H-14a), 1.63 (m, H-4'eq), 1.51 (m, H-2''b and H-7), 1.42 (m, H-14ax), 1.37 (s, 6-CH$_3$), 1.28 (d, 10-CH$_3$), 1.24 (d, 5''-CH$_3$), 1.19 (s, 3''-CH$_3$), 1.18 (d, 5'-CH$_3$), 1.12 (d, 2-CH$_3$), 1.11 (s, 12-CH$_3$), 1.08 (d, 8-CH$_3$), 1.04 (d, 4-CH$_3$), and 0.79 (t, CH$_2$CH$_3$).

$^1$H NMR (CD$_3$OD) δ 5.20 (br d, H-13), 4.50 (br d, H-1'), 4.16 (dq, H-5''), 4.02 (d, H-3), 3.70 (m, H-5'), 3.56 (br d, H-5), 3.34 (s, OCH$_3$), 3.25 (dd, H-2'), 3.03 (d, H-4''), 2.87 (m, H-8), 2.84 (m, H-2), 2.73 (m, H-3'), 2.44 (d, H-2''eq), 2.33 (s, N(CH$_3$)$_2$), 1.97 (m, H-4), 1.88 (m, H-14a), 1.73 (m, H-4'eq), 1.64 (m, H-7), 1.59 (dd, H-2''b), 1.47 (m, H-14ax), 1.36 (br s, 6-CH$_3$), 1.28 (d, 5''-CH$_3$), 1.24 (s, 3''-CH$_3$), 1.18 (m, 5'-CH$_3$, 2-CH$_3$, 8-CH$_3$ and 10-CH$_3$)), 1.13 (s, 12-CH$_3$), 1.08 (d, 4-CH$_3$), and 0.86 (t, CH$_2$CH$_3$).

$^{13}$C NMR (CDCl$_3$) δ 176.2, 168.2, 102.8, 95.9, 83.6 (br), 79.3 (br), 77.9, 77.3, 75.2, 75.1, 72.7, 71.0, 70.9, 68.8, 65.5, 65.3, 49.4, 40.2, 39.9 (br), 37.8 (br), 35.7 (br), 34.9, 34.1 (br), 28.9, 26.0 (br), 21.4, 21.3, 19.8 (br), 18.4, 16.8, 15.3 (br), 10.7, and 9.2.

$^{13}$C NMR (CD$_3$OD) δ 177.7, 170.0, 103.9, 97.7, 84.3 (br), 80.7, 79.2, 78.1, 77.0 (br), 76.1, 74.1, 72.8, 71.7 (br), 69.2, 66.7, 65.1, 49.9, 46.2 (br), 41.8 (br), 40.8, 40.5 (br), 36.0, 33.8 (br), 31.9, 26.7 (br), 22.8, 21.8, 21.7 (br), 21.6, 19.1, 17.5, 15.8 (br), 12.2 (br), 11.3, and 10.1.

FAB mass spectrum, m/z 749, 591, 416, 398, 174, 159, 158, and 116.

Elemental Analysis Calculated for C$_{37}$H$_{68}$N$_2$O$_{13}$: C, 59.34; H, 9.15; N, 3.74. Found: C, 59.12; H, 8.80; N, 3.82.

Method 2: 1.0 LiOH in EtOH (9E)-9-Deoxo-9-hydroxyiminoerythromycin A (255 mg, 0.34 mmol) was added to a solution of lithium hydroxide monohydrate (14.3 mg, 0.34 mmol) in absolute ethanol (2.55 mL). The resulting solution was stirred at room temperature for 25 hours, and then stored in a freezer at −20° C. for 68 hours. After warming to room temperature, the solution was evaporated under reduced pressure to remove the solvent. The residue was stirred with saturated aqueous sodium chloride (5 mL) and ethyl acetate (5 mL) while the pH was adjusted to 9.2 by addition of dilute hydrochloric acid. After shaking, the phases were separated and the aqueous portion extracted with more ethyl acetate (2× 2.5 mL). The combined ethyl acetate extracts were washed with saturated sodium chloride solution (4 mL), dried over magnesium sulfate, filtered and evaporated at reduced pressure to afford a white foam (263 mg). Examination of this material by $^1$H NMR spectroscopy revealed a 31:69 mixture of (9E)-9-deoxo-9-hydroxyiminoerythromycin A and (9Z)-9-deoxo-9-hydroxyiminoerythromycin A.

Method 3: 2.0 LiOH in EtOH (9E)-9-Deoxo-9-hydroxyiminoerythromycin A (291 mg, 0.333 mmol) was added to a solution of lithium hydroxide monohydrate (32.6 mg, 0.776 mmol) in absolute ethanol (2.9 mL). The resulting solution was stirred at room temperature under a nitrogen atmosphere for 22.5 hours. The solvent was evaporated at reduced pressure and the residue stirred with ethyl acetate (5 mL) and saturated aqueous sodium chloride (5 mL) while adjusting the pH to 9 by addition of 2N hydrochloric acid. The mixture was shaken, the phases separated, and the aqueous portion extracted with more ethyl acetate (2×2.5 mL). The combined ethyl acetate extracts were washed with saturated sodium chloride solution (4 mL), dried with magnesium sulfate, filtered and evaporated under vacuum to a white foam (299 mg). This material was shown by $^1$H NMR to be a 21:79 mixture of (9E)-9-deoxo-9-hydroxyiminoerythromycin A and (9Z)-9-deoxo-9-hydroxyiminoerythromycin A.

Method 4: 3.0 LiOH in EtOH (9E)-9-Deoxo-9-hydroxyiminoerythromycin A (239 mg, 0.319 mmol) was was added to a mixture of lithium hydroxide monohydrate (40.2 mg, 0.957 mmol) in absolute ethanol (2.4 mL), and the resulting solution was stirred at room temperature under a nitrogen atmosphere for 21.7 hours. Workup as described in method 3 afforded a white foam (236 mg) shown by $^1$H NMR to consist of a 19:81 mixture of (9E)-9-deoxo-9-hydroxyiminoerythromycin A and (9Z)-9-deoxo-9-hydroxyiminoerythromycin A.

Method 5: 2.0 NaOEt in EtOH

Freshly cut sodium metal (48 mg, 2.087 mmol) was dissolved in absolute ethanol (7.8 mL) under a nitrogen atmosphere. 9-Deoxo-9(E)-hydroxyiminoerythromycin A (782 mg, 1.043 mmol) was added and the resulting solution was stirred at room temperature. A crystalline precipitate, identified as the starting oxime by thin layer chromatography, appeared after a few hours. After stirring overnight, the mixture was once again a clear solution. After 54 hours, approximately half (3.9 mL) of the reaction mixture was removed and evaporated under reduced pressure. The gummy residue was stirred with ethyl acetate (5 mL) and saturated aqueous sodium chloride (5 mL) while the pH was adjusted to 9.2 by addition of dilute hydrochloric acid (2N and 0.2N solutions). The mixture was shaken, the layers separated, and the aqueous portion extracted with more ethyl acetate (2×2.5 mL). The combined ethyl acetate solution was washed with saturated brine (5 mL), dried with magnesium sulfate, filtered and evaporated under reduced pressure to a white foam (361 mg). This material was shown by $^1$H NMR spectroscopy to consist of a 22:78 mixture of the 9(E) and 9(Z) isomers of 9-deoxo-9-hydroxyiminoerythromycin A.

Method 6: 2.0 NaOH in EtOH

The remaining half of the reaction mixture from method 5 was treated with water (0.0188 mL, 1.04 mmol) to give a solution effectively consisting of sodium hydroxide and oxime in ethanol. The solution was stirred at room temperature for 23 hours, then worked up as described in method 5 to give a white foam (402 mg). This material was shown by $^1$H NMR to consist of a 24:76 mixture of the (9E) and (9Z) isomers of 9-deoxy-9-hydroxyiminoerythromycin A.

Method 7: 2.0 LiOH in MeOH

A solution of lithium hydroxide monohydrate (37 mg, 0.88 mmol), (9E)-9-deoxo-9-hydroxyiminoerythromycin A (330 mg, 0.44 mmol), and methanol (3.3 mL) was stirred at room temperature for 65.5 hours. The solution was then stored at −20° C. for 13 days before warming to room temperature and evaporating the solvent at reduced pressure. The residue was stirred with ethyl acetate (5 mL) and brine (5 mL) while adjusting the pH to 9.2 by addition of dilute hydrochloric acid. The mixture was shaken, the layers separated and the aqueous portion extracted with more ethyl acetate (2×2.5 mL). The combined ethyl acetate solution was washed with brine (5 mL), dried with magnesium sulfate, and evaporated under vacuum to provide a white foam (324 mg). NMR analysis of this material indicated a 45:55 ratio of (9E) to (9Z) 9-deoxo-9-hydroxyiminoerythromycin A products.

Method 8: 2.0 NaOMe in MeOH

A solution of (9E)-9-deoxo-9-hydroxyiminoerythromycin A (375 mg, 0.5 mmol) in anhydrous methanol (3.5 mL) was cooled in an ice bath and stirred under a nitrogen atmosphere while methanolic sodium methoxide (0.23 mL of a 25 wt % solution, 1.01 mmol) was added by syringe. The cooling bath was removed and the solution was stirred at room temperature and under a nitrogen atmosphere for 66 hours. The solution was then stored at −20° C. for 13.3 days before being processed to a white foam (329 mg) as described in method 7. The product consisted of a 35:65 mixture of (9E)-9-deoxo-9-hydroxyiminoerythromycin A and (9Z)-9-deoxo-9-hydroxyiminoerythromycin A as determined by $^1$H NMR spectroscopy.

Method 9: 10.0 NaOMe in MeOH

A solution of (9E)-9-deoxo-9-hydroxyiminoerythromycin A (100 mg, 0.134 mmol) in anhydrous methanol (4.70 mL) was treated with sodium methoxide (0.305 mL of a 25 wt % solution in methanol, 1.335 mmol) and stirred at room temperature for 74.5 hours. The solvent was evaporated under reduced pressure and the residue stirred with ethyl acetate (5 mL) and saturated brine (5 mL) while adjusting the pH of the aqueous layer to 9.4 with 2N hydrochloric acid. The mixture was shaken, the layers separated and the aqueous portion extracted with more ethyl acetate (2×2.5 mL). The combined ethyl acetate solution was washed with brine (5 mL), dried with magnesium sulfate, filtered and evaporated at reduced pressure to afford a white foam (102 mg). This material was shown by $^1$H NMR spectroscopy to consist of a 26:74 mixture of the (9E) and (9Z) isomers of 9-deoxo-9-hydroxyiminoerythromycin A.

Method 10: 2.0 LiOH in iPrOH (9E)-9-Deoxo-9-hydroxyiminoerythromycin A (279 mg, 0.361 mmol) was added to a partial solution of lithium hydroxide monohydrate (30.3 mg, 0.721 mmol) in isopropanol (2.7 mL), and the mixture was stirred at room temperature in a capped flask. A fine white precipitate formed in a few minutes and, after stiring overnight, the mixture was a hazy suspension. After 21 hours, the mixture was transferred to a freezer at −20° C. and stored there for 15 days. After warming to room temperature, the solvent was evaporated under vacuum and the residue stirred with ethyl acetate (5 mL) and brine (5 mL) while adjusting the pH to 9.2 with dilute hydrochloric acid. The mixture was shaken, the layers separated, and the aqueous phase extracted with more ethyl acetate (2×2.5 ml). The combined ethyl acetate solution was washed with brine (4 mL), dried with magnesium sulfate, filtered and evaporated under vacuum to afford a white foam (249 mg). The product consisted of a 26:74 mixture of (9E)-9-deoxo-9-hydroxyiminoerythromycin A and (9Z)-9-deoxo-9-hydroxyiminoerythromycin A as determined by $^1$H NMR spectroscopy.

Method 11: 1.0 LiOH in MeCN

A mixture of (9E)-9-deoxo-9-hydroxyiminoerythromycin A (500 mg, 0.668 mmol), lithium hydroxide monohydrate (28 mg, 0.668 mmol), and absolute ethanol (5 mL) was stirred at room temperature for 10 minutes to give a solution. The solution was evaporated under reduced pressure to afford a residue that was twice diluted with ethanol (10 mL) and evaporated at reduced pressure and then suspended in anhydrous acetonitrile (5 mL) and evaporated at reduced pressure. The solid residue was suspended in anhydrous acetonitrile (5 mL) and the mixture was stirred at room temperature for 18 days. The solvent was evaporated under reduced pressure and the residue was stirred with ethyl acetate (5 mL) and saturated aqueous sodium chloride solution (5 mL) while adjusting the pH of the aqueous phase to 9.5 by addition of dilute hydrochloric acid. The mixture was shaken, the layers separated, and the aqueous portion was extracted with additional ethyl acetate (2×2.5 mL). The combined ethyl acetate solution was washed with brine (5 mL), dried over magnesium sulfate, filtered and evaporated under reduced pressure to afford a foam (442 mg). This material was shown by $^1$H NMR spectroscopy to consist of a 44:56 mixture of the (9E) and (9Z) isomers of 9-deoxo-9-hydroxyiminoerythromycin A.

Method 12: 1.0 LiOH in DMF

A mixture of (9E)-9-deoxo-9-hydroxyiminoerythromycin A (500 mg, 0.668 mmol), lithium hydroxide monohydrate (28 mg), and dimethylformamide (5 mL) was stirred at room temperature in a capped flask. After a few hours, the initial suspension gave way to a solution. After stirring for 18 days and 18 hours, the solution was evaporated under reduced pressure and the residue was processed as described in method 11 to afford a foam (402 mg). Analysis of this material by $^1$H NMR spectroscopy indicated a 62:38 mixture of the (9E) and (9Z) isomers of 9-deoxo-9-hydroxyimioerythromycin A.

Method 13: 1.2 LiN(SiMe$_3$)$_2$ in MeCN

A suspension of (9E)-9-deoxo-9-hydroxyiminoerythromycin (500 mg, 0.668 mmol) in anhydrous acetonitrile (4 mL) was treated with lithium hexamethyldisilazide (0.80 mL of a 1M solution in hexane, 0.80 mmol). The resulting suspension rapidly gave way to a solution which reformed a suspension after stirring several days at room temperature. After 18 days and 19 hours, the reaction mixture was worked up as described in method 11 to afford a foam (423 mg). This material was shown by $^1$H NMR spectroscopy to be a 50:50 mixture of (9E)-9-deoxo-9-hydroxyiminoerythromycin A and (9Z)-9-deoxo-9-hydroxyiminoerythromycin A.

EXAMPLE 3

Crystallization of (9Z)-9-Deoxo-9-hydroxyiminoerythromycin A

A 3:1 mixture (30.0 g) of (9Z)-9-deoxo-9-hydroxyiminoerythromycin A and (9E)-9-deoxo-9-hydroxyiminoerythromycin A was added over 2 minutes to well stirred ethyl acetate (60 mL). After obtaining a solution, methylene chloride (120 mL) was rapidly added and the resulting suspension was stirred in an ice bath for one hour. The precipitate was filtered off, washed with methylene chloride (60 mL), and dried under a stream of nitrogen to afford an 86:14 mixture (26.5 g) of (9Z)-9-deoxo-9-hydroxyiminoerythromycin A and (9E)-9-deoxo-9-hydroxyiminoerythromycin A.

A solution of the above solid in ethyl acetate (60 mL) was diluted with methylene chloride (120 mL). The resulting suspension was cooled in an ice bath for one hour and then filtered. The collected solid was rinsed with methylene chloride (60 mL) and dried under a stream of nitrogen to afford a 95:5 mixture (23.4 g) of (9Z)-9-deoxo-9-hydroxyiminoerythromycin A and (9E)-9-deoxo-9-hydroxyiminoerythromycin A.

EXAMPLE 4

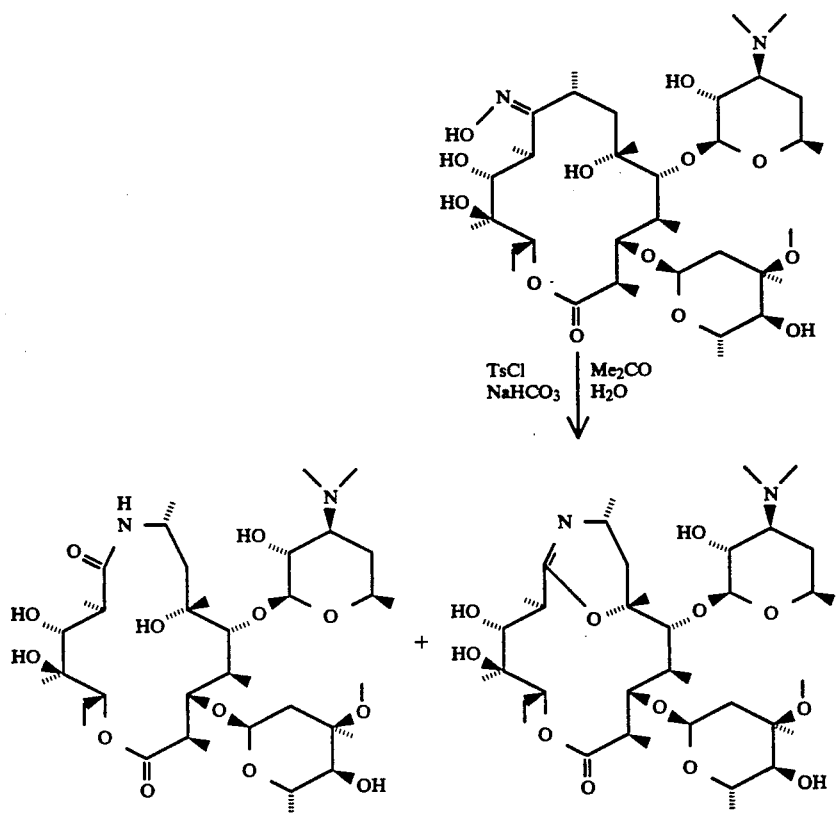

Synthesis of 8a-Aza-8a-homoerythromycin A and 9-Deoxo-6-deoxy-6,9-epoxy-8a,9-didehydro-8a-aza-8a-homoerythromycin A by the Beckmann Rearrangement of 9-Deoxo-9(Z)-hydroxyiminoerythromycin A Method 1

(9Z)-9-Deoxo-9-hydroxyiminoerythromycin A (200 mg, 0.27 mmol) was dissolved in acetone (2 mL) and the resulting solution was cooled in an ice-bath and stirred under a nitrogen atmosphere. A solution of sodium bicarbonate (84 mg, 1.0 mmol) in water (2 mL) was added followed by the dropwise addition of an acetone solution (2 mL) of p-toluenesulfonyl chloride (100 mg, 0.53 mmol) over 5 minutes.

After stirring for 1.5 hours at 0°–5° C., the mixture was diluted with dichloromethane (10 mL) and water (5 mL), and the pH was adjusted from 10 to 5.5 with 2N HCl. The dichloromethane layer was discarded and the aqueous layer was washed with additional dichloromethane (2×10 mL) which was also discarded. Dichloromethane (10 mL) was added to the aqueous layer and the pH was adjusted to 8.5 with 2.5N NaOH. The dichloromethane layer was removed and the aqueous layer was extracted with more dichloromethane (2×20 mL). The combined dichloromethane extracts were dried over anhydrous magnesium sulfate, filtered and evaporated under vacuum to give a mixture of the title compounds as a foam (150 mg).

The above mixture was purified by preparative layer chromatography (two 0.1 mm×20×20 cm Analtech silica gel GF plates, developing and eluting with 60:10:1 dichloromethane-methanol concentrated ammonium hydroxide) to afford 8a-aza-8a-homoerythromycin A (95 mg) and 9-deoxo-6-deoxy-6, 9-epoxy-8a, 9-didehydro-8a-aza-8a-homoerythromycin A (33 mg).

Method 2:

A solution of p-toluenesulfonyl chloride (1.00 g, 5.2 mmol) in acetone (20 mL) was added to a solution of sodium bicarbonate (0.90 g, 10.7 mmol) in water (20 mL). The resulting suspension was cooled in a −10° C. bath and stirred while a solution of (9Z)-9-deoxo-9-hydroxyiminoerythromycin A (2.00 g, 2.7 mmol) in acetone (20 mL) was added slowly over 75 minutes. The mixture was stirred at −10° C. for 5 hours, then warmed to 0° C. over 10 minutes and stirred at 0°–5° C. for 30 minutes. The mixture was evaporated under vacuum to remove the acetone. The aqueous residue was diluted with water (40 mL) and dichloromethane (60 mL) and stirred while the pH was adjusted to 5.5 with dilute hydrochloric acid. The aqueous layer was separated, washed with dichloromethane (60 mL), layered with dichloromethane (60 mL), and stirred while the pH was brought to 9 with dilute aqueous sodium hydroxide. The layers were separated and the aqueous portion extracted with more dichloromethane (2×50 mL). The combined pH 9 extracts were dried over magnesium sulfate, filtered and evaporated under reduced pressure to afford a gum (1.97 g) which was shown by $^1$H NMR spectroscopy to be a 1:1 mixture of 8a-aza-8a-homoerythromycin A and 9-deoxo-6-deoxy-6,9-epoxy-8a,9-didehydro-8a-aza-8a-homoerythromycin A.

The crude product mixture was dissolved in 120:10:1 dichloromethane-methanol-conc. aqueous ammonium hydroxide (5 mL) and loaded onto a column of silica gel (4×16 cm). The column was eluted with 120:10:1 dichloromethane-methanol-ammonium hydroxide. After a 150 mL forerun, 15 mL fractions were collected. Fractions 9-13 were combined and evaporated under vacuum to afford 9-deoxo-6-deoxy-6,9-epoxy-8a,9-didehydro-8a-aza-8a-homoerythromycin A (ca. 500 mg) and fractions 22-26 were combined and evaporated to afford 8a-aza-8a-homoerythromycin A (ca. 500 mg). The latter product was crystallized from ether to give the amide (ca. 130 mg) as a white solid.

Physical data for
9-deoxo-6-deoxy-6,9-epoxy-8a,9-didehydro-8a-aza-8a-homoerythromycin A IR (CHCl$_3$) 3550, 3440 (br), 2970, 2940, 2880, 1725, 1665, 1455, 1375, 1345, 1325, 1240, 1170, 1105, 1080, 1050, 1015, 995, and 955 cm−1.

$^1$H NMR (CDCl$_3$) δ 5.02 (d, H-1″), 4.90 (dd, H-13), 4.48 (d, H-1′), 4.09 (dq, H-5″), 4.02 (t, H-3), 3.81 (d, H-5), 3.53 (m, H-5′), 3.49 (d, H-11), 3.43 (m, H-8), 3.35 (s, OCH$_3$), 3.20 (dd, H-2′), 3.07 (t, H-4″), 2.75 (dq, H-2), 2.68 (dq, H-10), 2.52 (ddd, H-3′), 2.43 (d, H-2″eq), 2.28 (s, N(CH$_3$)2), 1.98 (ddq, H-4), 1.91 (m, H-14a), 1.90 (dd, H-7a), 1.68 (ddd, H-4′eq), 1.62 (dd, H-2″ax), 1.46 (m, H-14b), 1.39 (s, 6-CH$_3$), 1.32 (d, 5″-CH$_3$), 1.27 (s, 3″-CH$_3$), 1.24 (m, H-7b), 1.22 (d, 5′-CH$_3$), 1.21 (m, H-4′ax), 1.16 (d, 10-CH$_3$), 1.15 (d, 8-CH$_3$), 1.15 (s, 12-CH$_3$), 1.14 (d, 2-CH$_3$), 1.08 (d, 4-CH$_3$), and 0.87 (t, CH$_2$CH$_3$).

$^{13}$C NMR (CDCl$_3$) δ 177.6, 160.6, 102.4, 94.6, 80.1, 78.9, 77.9, 77.4, 76.5, 75.7, 73.0, 70.6, 70.0, 68.8, 65.8, 65.6, 49.4, 44.9, 44.0, 42.3, 42.1, 40.3, 34.5, 32.0, 28.5, 23.8, 22.4, 21.5, 21.3, 21.0, 18.2, 17.0, 16.4, 12.5, 10.8, and 8.4.

FAB mass spectrum, m/z 731, 713, 602, 573, 555, 398, 159, 158, and 116.

Physical data for 8a-aza-8a-homoerythromycin A

MP 170°-176° C.

IR (CHCl$_3$) 3500 (br), 3430, 3320, 2970, 2935, 2880, 1730, 1630, 1560, 1525, 1455, 1375, 1325, 1280, 1170, 1160, 1105, 1085, 1045, 1010 and 995 cm−1.

$^1$H NMR (CDCl$_3$) δ 5.89 (br d, NH), 5.07 (d, H-1″), 4.92 (dd, H-13), 4.43 (d, H-1′), 4.35 (d, H-3), 4.21 (m, H-8), 4.01 (dq, H-5″), 3.58 (d, H-5), 3.50 (m, H-5′), 3.50 (s, H-11), 3.32 (s, OCH$_3$), 3.21 (dd, H-2′), 3.03 (t, H-4″), 2.62 (dq, H-2), 2.54 (m, H-3′), 2.35 (m, H-10), 2.35 (s, N(CH$_3$)2), 2.31 (d, H-2″eq), 1.90 (m, H-4), 1.89 (m, H-14a), 1.75 (br d, H-4′eq), 1.57 (dd, H-2″ax), 1.51 (m, H-7a and H-7b), 1.44 (m, H-14b), 1.43 (s, 6-CH$_3$), 1.30 (d, 5″-CH$_3$), 1.24 (s, 3″-CH$_3$), 1.23 (m, H-4′ax), 1.23 (d, 5′-CH$_3$), 1.20 (d, 8-CH$_3$), 1.19 (d, 10-CH$_3$), 1.18 (d, 2-CH$_3$), 1.09 (s, 12-CH$_3$), 1.05 (d, 4-CH$_3$), and 0.89 (t, CH$_2$CH$_3$).

$^{13}$C NMR (CDCl$_3$) δ 177.6, 176.6, 102.7, 94.2, 83.0, 77.9, 77.0, 76.6, 74.6, 73.7, 72.9, 70.0, 69.8, 68.8, 65.8, 65.2, 49.2, 45.8, 43.2, 42.4, 41.0, 40.4, 40.1, 34.5, 28.3, 27.6, 23.1, 21.7, 21.5, 21.2, 18.0, 16.1, 14.6, 11.2, 10.0, and 9.1.

Mass Spectrum, m/z 749, 731, 591, 589, 573, 416, 174, 159, 158 and 117.

Elemental Analysis: Calculated for C$_{37}$H$_{68}$N$_2$O$_{13}$: C, 59.34; H, 9.15; N, 3.74. Found: C, 59.24; H, 9.15; N, 3.44. Loss on drying at 120° C., 3.11%.

EXAMPLE 5

Synthesis of
9-Deoxo-6-deoxy-6,9-epoxy-8a,9-didehydro-8a-aza-8a-homoerythromycin A and
9-Deoxo-12-deoxy-9,12-epoxy-8a,
9-didehydro-8a-aza-8a-homoerythromycin A by Beckmann Rearrangement of
(9Z)-9-Deoxo-9-hydroximinoerythromycin A

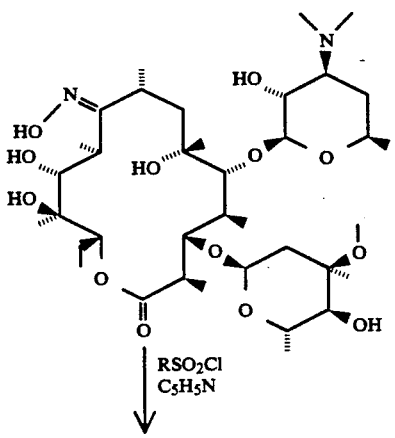

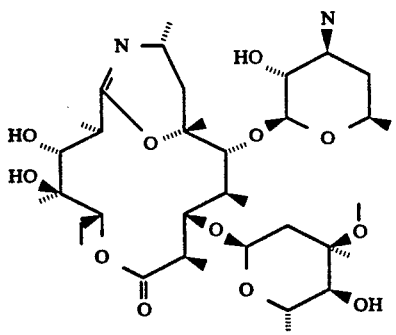 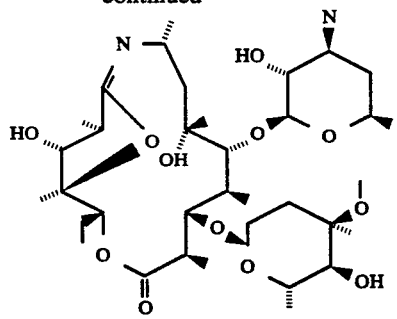

Method 1

A solution of p-toluenesulfonyl chloride (15.0 g, 0.079 mol) in diethyl ether (50 mL) was added dropwise over 8 minutes to an ice-cold, stirring solution of (9Z)-9-deoxo-9-hydroxyiminoery thromycin A (23.2 g, 0.031 mol) in pyridine (180 mL). the resulting solution was stirred at 0°–5° C. for 2.5 hours, then diluted with dichloromethane (400 mL) and water (500 mL) and basified to pH 9.5 by addition of 5N sodium hydroxide. The layers were separated and the aqueous portion extracted with more dichloromethane (200 mL, 100 mL). The combined dichloromethane extracts were dried over magnesium sulfate, filtered, and evaporated under vacuum to afford an oil. Residual pyridine was removed by twice taking the product up in toluene (100 mL) and evaporating the solvent under vacuum. The resulting foam (21.4 g) was shown by $^1$H NMR spectroscopy to be a 26:74 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.

Method 2

A solution of p-toluenesulfonyl chloride (160 mg, 0.84 mmol) in diethyl ether (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0°–5° C. for 1.5 hours, then diluted with dichloromethane (4 mL) and water (4 mL) and basified to pH 9.5 by addition of 5N sodium hydroxide. The layers were separated and the aqueous portion extracted with more dichloromethane (2×4 mL). The combined dichloromethane extracts were dried over magnesium sulfate, filtered, evaporated under vacuum and stripped with hexane (4×15 mL) to afford a yellow solid (260 mg). This material was shown by 1H NMR spectroscopy to be a 25:75 mixture of 9-deoxo-6-deoxy-6,9-epoxy- and 9-deoxo-12-deoxy-9,12-epoxy-8a,9-dide-hydro-8a-aza-8a-homoerythromycin A.

Method 3

A solution of p-toluenesulfonyl chloride (160 mg, 0.84 mmol) in acetonitrile (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0°–5° C. for 80 minutes, then diluted with dichloromethane (4 mL) and water (5 mL) and basified to pH 9.5 by addition of 5N sodium hydroxide. The layers were separated and the aqueous portion extracted with more dichloromethane (2×4 mL). The combined dichloromethane extracts were dried over magnesium sulfate, filtered, and evaporated under vacuum to a foam which was stripped with toluene (2×10 mL) and hexanes (10 mL) to afford a solid (230 mg). This material was shown by 1H NMR spectroscopy to be a 33:67 mixture of 9-deoxo-6-deoxy-6,9-epoxy-and 9-deoxo-12-deoxy-9,12-epoxy-8a,9-didehydro-8a-aza-8a-homoerythromycin A.

Method 4

A solution of p-toluenesulfonyl chloride (160 mg, 0.84 mmol) in toluene (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0°–5° C. for 90 minutes, then diluted with dichloromethane (4 mL) and water (4 mL) and basified to pH 9.5 by addition of 1N sodium hydroxide. The layers were separated and the aqueous portion extracted with more dichloromethane (3×4 mL). The combined dichloromethane extracts were dried over magnesium sulfate, filtered, and evaporated under vacuum to a solid (250 mg). This material was shown by 1H NMR spectroscopy to be a 27:73 mixture of 9-deoxo-6-deoxy-6,9-epoxy- and 9-deoxo-12-deoxy-9,12-epoxy-8a,9-didehydro-8a-aza-8a-homoerythromycin A.

Method 5

Benezenesulfonyl chloride (0.107 mL, 0.84 mmol) was added by syringe to an ice-cold solution of (9Z)-9-deoxo-9-hydroxyiminoerythromycin A (250 mg, 0.33 mmol) in pyridine (2.0 mL). The resulting solution was stirred at 0°–5° C. for 75 minutes, then processed as described above to afford a yellow solid (240 mg). This material was shown by 1H NMR spectroscopy to be a 31:69 mixture of 9-deoxo-6-deoxy-6,9-epoxy- and 9-deoxo-12-deoxy-9,12-epoxy-8a,9-didehydro-8a-aza-8a-homoerythromycin A.

Method 6

Methanesulfonyl chloride (0.065 mL, 0.84 mmol) was added by syringe to an ice-cold solution of (9Z)-9-deoxo-9-hydroxyiminoerythromycin A (250 mg, 0.33 mmol) in pyridine (2.0 mL). The resulting solution was stirred at 0°–5° C. for 2 hours, then processed as described above to afford an off-white solid (246 mg). This material was shown by $^1$H NMR spectroscopy to be a 25:70:5 mixture of 9-deoxo-6-deoxy-6,9-epoxy-8a,9-didehydro-8a-aza-8a-homoerythromycin A, 9-deoxo-12-deoxy-9,12-epoxy-8a,9-didehydro-8a-aza-8a-homoerythromycin A, and 9-deoxy-9,12-epoxy-4''-O-methanesulfonyl-8a,9-didehydro-8a-aza-8a-homoerythromycin A.

Method 7

A solution of (9Z)-9-deoxo-9-hydroxy-iminoerythromycin A (250 mg, 0.33 mmol) in pyridine (2.0 mL) was cooled in a −20° C. bath and treated with methanesulfonyl chloride (0.071 mL, 0.92 mmol). The resulting hazy solution was stirred at −10° to −20° C. for 90 minutes, then processed as described above to afford a yellow solid (254 mg). This material was shown by 1H NMR spectroscopy to be a 88:12 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.

Method 8

A mixture of (9Z)-9-deoxo-9-hydroxyiminoerythromycin A (0.50 g, 0.67 mmol), p-toluenesulfonyl chloride (318 mg, 1.67 mmol) and pyridine (0.162 mL, 2.0 mmol) in dichloromethane (5.0 mL) was stirred at room temperature for 1.5 hours. The mixture was diluted with water and stirred rapidly while adjusting the pH to 11 with 5N sodium hydroxide. The organic phase was separated, dried with magnesium sulfate, filtered and evaporated under reduced pressure to afford a yellow solid (570 mg). Analysis of the crude product by $^1$H NMR spectroscopy revealed a 80:20 mixture of 9-deoxo-6,9-epoxy-8a,9-didehydro-8a-aza-8a-homoerythromycin A and 9-deoxo-9,12-epoxy-8a,9-didehydro-8a-aza-8a-homoerythromycin A.

Purification of 9-Deoxo-12-deoxy-9,12-epoxy-8a,9-didehydro-8a-aza-8a-homoerythromycin A by Column Chromatography The following procedure illustrates the purification process for 9-deoxo-12-deoxy-9,12-epoxy-8a,9-didehydro-8a-aza-8a-homoerythromycin A.

The crude products from methods 3 and 4 above were combined, dissolved in 94:5:1 dichloromethane-methanol-triethylamine, and loaded onto a column of silica gel (230–400 mesh, 2.5×24.5 cm, wet packed under 94:5:1 dichloromethane-methanol-triethylamine). The column was eluted with 94:5:1 dichloromethane-methanol-triethylamine, collecting 6 mL fractions. Fractions 15–18 were combined, evaporated under reduced pressure, and the residue twice stripped with toluene to provide 9-deoxo-12-deoxy-9,12-epoxy-8a,9-didehydro-8a-aza-8a-homoerythromycin A (190 mg) as a foam. The product is a mixture of major and minor forms as ascertained by $^1$H and $^{13}$C NMR spectroscopy.

IR (CHCl$_3$) 3550, 3390 (br), 2975, 2940, 2880, 1735, 1690, 1455, 1375, 1240, 1165, 1085, 1045, 1010, and 970 cm$^{-1}$.

FAB mass spectrum, m/z 731, 713, 602, 573, 556, and 158.

Chromatographic Separation of 9-Deoxo-6-deoxy-6,9-epoxy-8a,9-didehydro-8a-aza-8a-homoerythromycin A and 9-Deoxo-12-deoxy-9,12-epoxy-8a,9-didehydro-8a-aza-8a-homoerythromycin A and Crystallization of 9-Deoxo-12-deoxy-9,12-epoxy-8a,9-didehydro-8a-aza-8a-homoerthromycin A A sample (4.0 g) of the crude product mixture obtained as described in method 1 was dissolved in 60:10:1 dichloromethane-methanol-conc. aqueous ammonium hydroxide (6 mL) and the solution was loaded onto a column of EM silica gel 60 (4.5×18 cm, 230–400 mesh, wet packed under 60:10:1 dichloromethane-methanol-conc. ammonium hydroxide). The column was eluted with 60:10:1 dichloromethane-methanol-conc. aqueous ammonium hydroxide. The fractions collected from 150 mL to 165 mL of eluant were evaporated under vacuum to afford 9-deoxo-6-deoxy-6,9-epoxy-8a,9-didehydro-8a-aza-8a-homoerythromycin A (0.34 g) as a foam. The fractions collected from 185 mL to 285 mL of eluant were combined and evaporated under reduced pressure to afford a mixture of the two isomeric forms of 9-deoxo-12-deoxy-9,12-epoxy-8a,9-didehydro-8a-aza-8a-homoerythromycin A (1.36 g) as a foam.

A solution of the mixture of 9,12-epoxy isomers in nitromethane (2 mL) deposited a large, crystalline mass on standing at room temperature for several days. The mixture was diluted with nitromethane (10 mL) and filtered to remove the solid portion, which was washed with nitromethane (2 mL) and dried under high vacuum. The white solid thus obtained (0.9 g) was shown by $^1$H NMR spectroscopy to be the major 9,12-epoxy isomer which is initially formed in the Beckmann rearrangement reaction. While stable in the solid state, solutions of the crystalline isomer in chloroform-d equilibrate at room temperature in several hours to a 1:1 mixture of the two isomers of 9-deoxo-12-deoxy-6,9-epoxy-8a,9-didehydro-8a-aza-8a-homoerthromycin A.

Physical data for 9-deoxo-12-deoxy-9,12-epoxy-8a,9-didehydro-8a-aza-8a-homoerythromycin A:

Isomer A (crystalline isomer)
MP 124°–130° C. (slowly softens).

IR (CHCl$_3$) 3350, 3380 (br), 2970, 2935, 2875, 1735, 1695, 1560, 1460, 1375, 1250, 1165, 1115, 1085, 1045, 1015, and 975 cm$^{-1}$.

$^1$H NMR (CDCl$_3$) δ 5.17 (dd, H-13), 4.73 (d, H-1″), 4.47 (d, H-1′), 4.15 (dq, H-5″), 4.09 (dd, H-3), 3.99 (br s, H-5), 3.81 (t, H-11), 3.68 (m, H-8), 3.65 (m, H-5′), 3.40 (ddd, H-2′), 3.23 (s, OCH$_3$), 2.96 (t, H-4″), 2.70 (p, H-10), 2.68 (m, H-3′), 2.57 (br d, 11-OH), 2.45 (p, H-2), 2.31 (s, N(CH$_3$)$_2$), 2.28 (d, H-2″eq), 2.20 (d, 4″-OH), 2.07 (ddq, H-14a), 1.90 (br d, H-7a), 1.75 (dd, H-7b), 1.74 (m, H-4), 1.70 (m, H-4′eq), 1.69 (m, H-14b), 1.46 (dd, H-2″ax), 1.40 (s, 6-CH$_3$), 1.29 (m, H-4′ax), 1.27 (d, 10-CH$_3$), 1.27 (d, 5″-CH$_3$), 1.25 (d, 2-CH$_3$), 1.24 (d, 5′-CH$_3$), 1.21 (s, 3″-CH$_3$), 1.18 (s, 12-CH$_3$), 1.07 (d, 8-CH$_3$), 1.01 (d, 4-CH$_3$), and 0.86 (t, CH$_2$CH$_3$).

$^{13}$C NMR (CDCl$_3$) δ 174.2, 161.3, 106.7, 98.3, 85.4, 84.2, 80.5, 79.8, 77.4, 75.0, 72.3, 70.3, 69.4, 66.3, 63.8, 49.4, 49.2, 49.0, 47.1, 45.4, 43.2, 40.4, 35.0, 29.3, 27.5, 24.6, 24.4, 23.3, 21.4, 21.0, 17.6, 17.2, 16.9, 11.3, and 11.2.

Elemental Analysis Calculated for C$_{37}$H$_{66}$N$_2$O$_{12}$: C, 60.80; H, 9.10; N, 3.83. Found: C, 60.71; H, 9.38; N, 3.78.

Loss on drying at 120° C., 2.82%.

Isomer B $^1$H NMR (CDCl$_3$) δ 5.20 (dd, H-13), 4.74 (d, H-1″), 4.48 (d, H-1′), 4.17 (t, H-3), 4.15 (m, H-5″), 4.11 (dd, H-11), 3.97 (m, H-8), 3.71 (d, H-4), 3.62 (m, H-5′), 3.30 (br dd, H-2′), 3.23 (s, OCH$_3$), 2.97 (t, H-4″), 2.88 (d, 11-OH), 2.85 (p, H-10), 2.60 (m, H-3′), 2.46 (p, H-2), 2.28 (s, N(CH$_3$)$_2$), 2.27 (d, H-2″eq), 2.23 (d, 4″-OH), 1.98 (ddq, H-14a), 1.84 (dd, H-7a), 1.77 (m, H-4), 1.76 (m, H-14b), 1.66 (m, H-4′eq), 1.64 (dd, H-7b), 1.49 (dd, H-2″ax), 1.29 (s, 6-CH$_3$), 1.27 (d, 5″-CH$_3$), 1.24 (d, 2-CH$_3$), 1.22 (d, 5′-CH$_3$), 1.19 (d, 10-CH$_3$), 1.19 (s, 3″-CH$_3$), 1.14 (s, 12-CH$_3$), 1.09 (d, 8-CH$_3$), 1.09 (d, 4-CH$_3$), and 0.94 (t, CH$_2$Ce,uns/H/$_3$).

$^{13}$C NMR (CDCl$_3$) δ 174.4, 160.5, 104.6, 97.0, 86.2, 79.1, 78.6, 77.7, 77.4, 75.1, 70.5, 69.4, 66.0, 64.7, 49.4, 48.2, 47.7, 47.4, 42.3, 40.4, 34.9, 29.1, 25.6, 24.0, 23.6, 22.9, 21.5, 21.0, 15.8, 11.7, 10.7, and 9.6.

EXAMPLE 6

Synthesis of 8a-Aza-8a-allyl-8a-homoerythromycin A

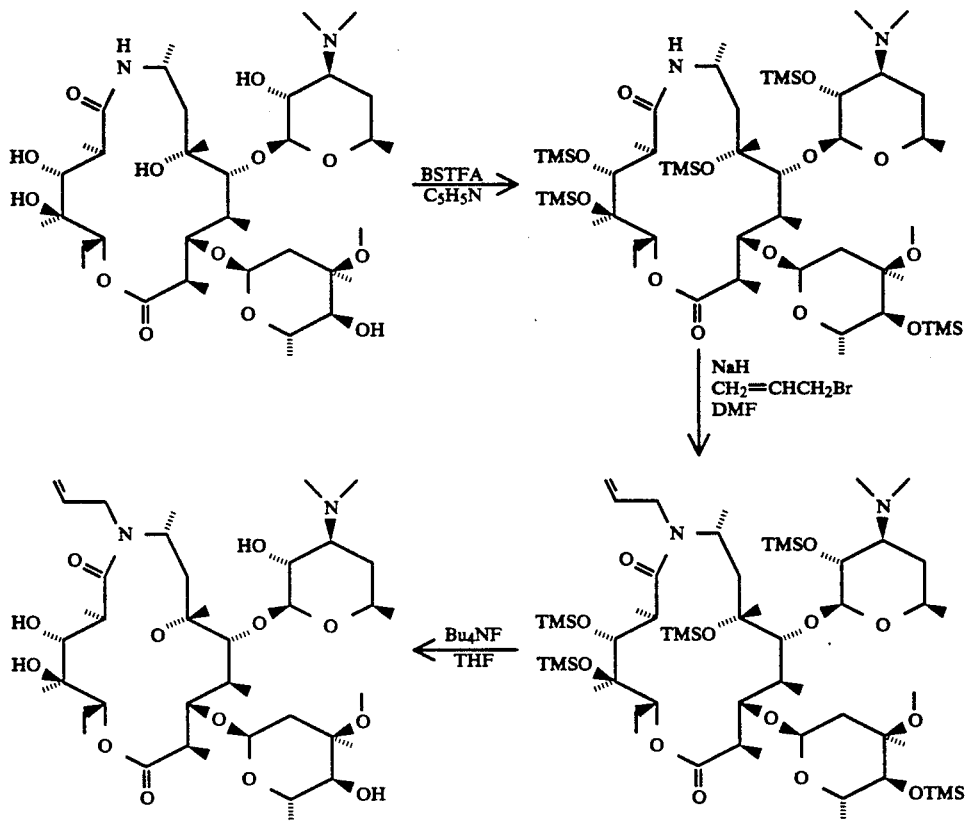

Step 1:
2'-0.4''-0.6-0.11-0.12-0-Penta(trimethylsilyl)-8a-aza-8a-homoerythromycin A 8a-Aza-8a-homoerythromycin A (748 mg, 1 mmol) is added to a mixture of pyridine (2 mL, 24.7 mmol) and bis(trimethylsilyl) trifluoroacetamide (2 mL, 7.5 mmol) and the resulting solution is stirred at room temperature for 48 hours. The mixture is evaporated under vacuum and the residue is three times diluted with toluene (40 mL each) and evaporated under vacuum. The residue is dissolved in 1:1 hexane-diethylether (1 mL) and loaded onto a column of EM silica gel 60 (2.5×24 cm, 230-400 mesh, wet packed with 1:1 hexane-diethylether). The column is eluted with 1:1 hexane-diethylether, collecting 10 mL fractions. The appropriate fractions are combined and evaporated under vacuum. The residue is lyophilized from benzene to afford the title compound.

Step 2:
2'-0.4''-0.6-0.11-0.12-0-Penta(trimethylsilyl)-8a-aza-ally-8a-homoerythromycin A 2'-0,4''-0,6-0,11-0,12-0-Penta(trimethylsilyl)-8a-aza-8a-homoerythromycin A (200 mg, 0.18 mmol) is dissolved in anhydrous dimethylformamide (0.5 mL) and the solution is treated with sodium hydride (5.5 mg of a 80% dispersion in mineral oil, 0.184 mmol). The suspension is blanketed with nitrogen and stirred at room temperature for 2 hours. The reaction mixture is cooled in an ice bath and treated with allyl bromide (0.016 mL, 0.18 mmol). After stirring for two hours, the reaction mixture is removed from the ice-bath and is allowed to warm to room temperature. After stirring an additional two hours, the solution is evaporated under vacuum and the residue is partitioned between methylene chloride (5 mL) and water (5 mL). The aqueous layer is re-extracted and the combined methylene chloride extracts are dried with magnesium sulfate, filtered and evaporated to give the crude product. The title compound is purified by column chromatography on EM silica gel 60 (2.5×24 cm, 230-400 mesh, wet packed with 1:1 hexane-diethylether). The column is eluted with 1:1 hexanediethylether, collecting 10 mL fractions. The appropriate fractions are combined, evaporated and lyophilized from benzene to afford the title compound.

Step 3: 8a-Aza-8a-allyl-8a-homoerythromycin A

2'-0,4''-0,6-0,11-0,12-0-Penta(trimethylsilyl)-8a-aza-8a-allyl-8a-homoerythromycin A (200 mg, 0.17 mmol) is dissolved in anhydrous tetrahydrofuran (1 mL) and the resulting solution is treated with tetrabutylammonium fluoride (0.5 mL of a 3.4M solution in THF, 1.7 mmol). The solution is blanketed with nitrogen and stirred 18 hours at room temperature. The solution is added to a well stirred mixture of methylene chloride (5 mL) and water (5 mL), and the pH is adjusted to 4 with 2N hydrochloric acid. The methylene chloride layer is removed and the aqueous layer is washed with additional methylene chloride (3×5 mL). Methylene chloride (5 mL) is added to the aqueous phase and the mixture is stirred rapidly while the pH is adjusted to 10 with 2N sodium hydroxide. The methylene chloride layer is separated and the aqueous layer is re-extracted with additional methylene chloride (3×5 mL). The combined pH 10 methylene chloride extracts are dried with magnesium sulfate, filtered and evaporated under vacuum to afford the title compound.

EXAMPLE 7

Synthesis of 8a-Aza-8a-methyl-8a-homoerythromycin A peroxide (1.9 mL, 18.6 mmol) and the mixture is stirred at room temperature for 6 hours. The solution is added to an ice cooled mixture of water (100 mL) and dichloromethane (100 mL) and the excess oxidant is destroyed by the careful addition of a saturated aqueous solution of sodium sulfite. The phases are separated and the aqueous layer is re-extracted with more dichloromethane (25 mL). The combined extracts are dried with magnesium sulfate, filtered, and evaporated under vac-

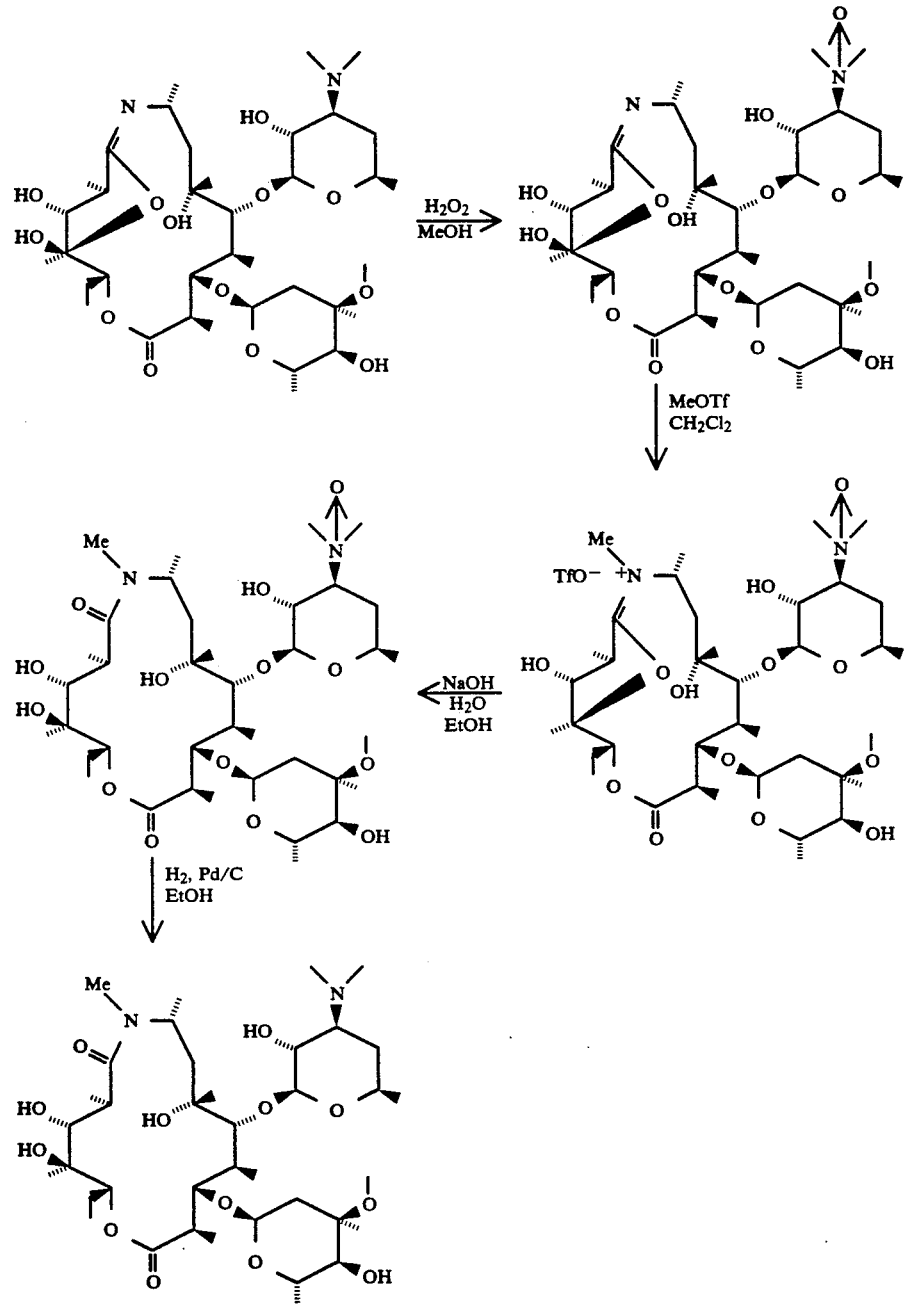

Step 1:
9-Deoxo-12-deoxy-9,12-epoxy-8a,9-didehydro-8a-aza-8a-homoerythromycin A 3'-N-oxide 9-Deoxo-12-deoxy-9,12-epoxy-8a,9-didehydro-8a-aza-8a-homoerythromycin A (3.0 g, 4.1 mmol) in methanol (24 mL) is treated with 30% aqueous hydrogen uum to give the title compound.

Step 2:
9-Deoxo-12-deoxy-9,12-epoxy-8a,9-didehydro-8a-aza-8a-methyl-8a-homoerythromycin A 3'-N-oxide trifluoromethanesulphonate 9-Deoxo-12-deoxy-9,12-epoxy-8a,9-didehydro-8a-aza-8a-homoerythromycin A 3'-N-oxide (1.0 g, 1.34 mmol) is dissolved in anhydrous dichloromethane (10 mL) and the solution is treated with methyl trifluoromethanesulfonate (0.158 mL, 1.4 mmol) over 5 minutes. After stirring two hours at room temperature, the solvent is evaporated under vacuum to afford the title compound.

Step 3: 8a-Aza-8a-methyl-8a-homoerythromycin A 3'-N-oxide

9-Deoxo-12-deoxy-9,12-epoxy-8a,9-didehydro-8a-aza-8a-methyl-8a-homoerythromycin A 3'-N-oxide trifluoromethanesulphonate (455 mg, 0.5 mmol) is added to a stirred solution of sodium hydroxide (22 mg, 0.55 mmol) in 50% aqueous ethanol (5 mL). The solution is blanketed with nitrogen and stirred overnight at room temperature. The reaction mixture is evaporated under vacuum and the residue is partitioned between water (10 mL) and dichloromethane (10 mL). The dichloromethane portion is dried with magnesium sulfate, filtered and evaporated under vacuum to give the title compound.

Step 4: 8a-Aza-8a-methyl-8a-homoerythromycin A

8a-Aza-8a-methyl-8a-homoerythromycin A 3'-N-oxide (100 mg, 0.11 mmol) is dissolved in ethanol (5 mL) and the mixture is hydrogenated for 2 hours at 40 psi in the presence of 10% palladium on carbon (100 mg). The suspension is filtered and the filtrate is evaporated under reduced pressure. The residue is dissolved in 90:10:1 dichloromethane-methanol-concentrated ammonium hydroxide (1 mL) and loaded onto a column of EM silica gel 60 (230-400 mesh, 2.5×24 cm, wet packed with 90:10:1 dichloromethane-methanol-concentrated ammonium hyroxide). The column is eluted with 90:10:1 dichloromethane-methanol-concentrated ammonium hydroxide, collecting 6 mL fractions. The product containing fractions are located by thin layer chromatography, combined and evaporated under vacuum to afford the title compound.

The test procedures employed to measure the activity of the compounds of the invention are described below.

EXAMPLE 8

The compounds of formula (II) will show antibacterial activity against a range of aerobic Gram positive and negative bacteria as shown in the following Table. The assay employs a liquid turbidimetric microtiter method for determination of the minimum inhibitory concentration (MIC) in broth media. The MIC endpoint in mcg/ml is defined as the lowest concentration of test compound that completely inhibits the growth (absence of detectable turbidity) of bacteria. The MIC is generally not an absolute value but rather a concentration range that falls within a two-fold dilution limit. Generally, twelve two-fold dilutions of the test compound are employed with the initial concentration set at 128 mcg/ml.

TABLE I

In vitro Activity

| Microorganism | | MIC Values (mcg/ml) |
|---|---|---|
| Enterococcus faecalis | MB 5407 | 16 |
| Enterococcus faecium | MB 5416 | ≦0.06 |
| Streptococcus agalactiae | CL 1343 | 0.25 |
| Staphylococcus aureus | MB 2865 | 1 |
| Staphylococcus epidermidis | MB 5414 | 2 |
| Staphylococcus haemolyticus | MB 5412 | 2 |
| Steptococcus pneumoniae | CL 2883 | ≦0.06 |
| Streptococcus pyogenes | MB 2874 | ≦0.06 |
| Streptococcus pyogenes | MB 5406 | 128 |
| Streptococcus viridans | CL 2943 | 4 |
| Escherichia coli | MB 2884 | 32 |
| Escherichia coli | MB 4926 | 4 |
| Klebsiella pneumoniae | MB 4005 | 64 |
| Yersinia enterocoltica | CL 1598 | 64 |
| Pseudomonas stutzeri | MB 1231 | 0.12 |

Values given are for 8a-aza-8a-homoerythromycin A, the product of Example 4.

The compounds of formula (II) are useful as antibacterial agents both in vitro and in vivo, and their spectrum of activity is similar to that of erythromycin A. Consequently, they can be used for the same purposes, and, in the same manner, as erythromycin A. In general, the antibacterial compounds of formula II and salts thereof, exhibit in vitro activity against a variety of Gram-positive microorganisms, e.g. Streptococcus pyogenes and Staphylococcus aureaus, and against certain Gram-negative microorganisms such as those of spherical or ellipsoidal shape (cocci). Their activity is readily demonstrated by in vitro tests against various microorganisms. Their in vitro activity renders them useful for topical application; for sterilization purposes, e.g., sickroom utensils; and as industrial antimicrobials, for example, in water treatment, slime control, and preservation of paint and wood. The extrapolation of such in vitro tests to support for such utilities for macrolide compounds is taught in U.S. Pat. No. 4,518,590. For in vitro use for topical application, it will usually be convenient to prepare pharmaceutical composition, in which a compound is combined with a pharamaceutically acceptable carrier or diluent, for example, in the form of ointments and creams. Appropriate carriers and diluents for these purposes include mineral oils and vegetable oils, and solvents such as water, alcohols, and glycols, and mixtures thereof. Such a pharmaceutical composition will normally contain the pharmaceutically-acceptable carrier and a compound of formula II in a weight ratio in the range from 1:4 to 1:200.

Additionally, the antibacterial compounds of formula II and the pharmaceutically-acceptable salts thereof are active in vivo versus a variety of Gram-positive microorganisms, e.g. Streptococcus pyogenes and Staphylococcus aureaus, and also certain Gram-negative microorganisms, via the oral and parenteral routes of administration in animals, including man. Their in vivo activity is more limited than their in vitro activity as regards susceptible organisms, and it is determined by the usual procedure which comprises infecting mice of substantially uniform weight with the test organism and subsequently treating them orally or subcutaneously with the test compound. Extrapolation of such in vivo tests to support for human utility for macrolide compounds is likewise taught in U.S. Pat. No. 4,518,590, cited above.

While the invention has been described and illustrated in reference to certain preferred embodiments thereof, those skilled in the art will appreciate that various changes, modifications and substitutions can be made therein without departing from the spirit and scope of the invention.

It is intended, therefore, that the invention be limited only by the scope of the claims which follow and that such claims be interpreted as broadly as is reasonable.

What is claimed is:

1. A compound of the formula:

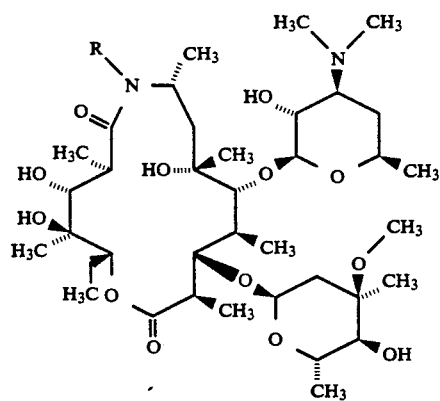

and the pharmaceutically acceptable salts and esters thereof, wherein R is hydrogen or C$_{1-10}$ alkyl.

2. A compound of the formula:

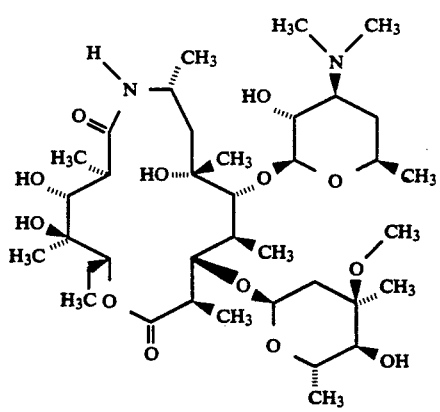

and the pharmaceutically acceptable salts and esters thereof.

3. A compound of the formula

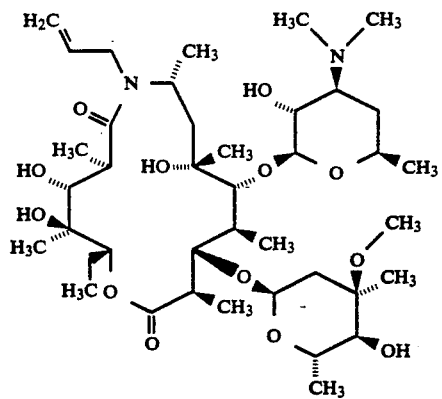

and the pharmaceutically acceptable salts and esters thereof.

4. A compound of the formula and the pharmaceutically acceptable salts and esters thereof.

* * * * *